(12) United States Patent
Bednarek et al.

(10) Patent No.: US 7,691,095 B2
(45) Date of Patent: Apr. 6, 2010

(54) BI-DIRECTIONAL STEERABLE CATHETER CONTROL HANDLE

(75) Inventors: Michael C. Bednarek, Buffalo, MN (US); Eric J. Wilkowske, North Oaks, MN (US); Richard E. Stehr, Stillwater, MN (US); William Emerson Butler, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1452 days.

(21) Appl. No.: 11/023,667

(22) Filed: Dec. 28, 2004

(65) Prior Publication Data

US 2006/0142694 A1    Jun. 29, 2006

(51) Int. Cl.
*A61M 25/00* (2006.01)
(52) U.S. Cl. .............. 604/523; 604/95.01; 604/524; 604/525; 604/528; 604/529; 604/264; 600/585
(58) Field of Classification Search .......... 600/585; 604/523, 528, 529, 95.01, 264
See application file for complete search history.

(56) References Cited

U.S. PATENT DOCUMENTS

| | | | |
|---|---|---|---|
| 3,375,583 A * | 4/1968 | Blank et al. ............... 433/86 |
| 4,960,134 A | 10/1990 | Webster, Jr. .............. 128/786 |
| 5,125,895 A | 6/1992 | Buchbinder et al. ......... 604/95 |
| 5,125,896 A | 6/1992 | Hojeibane ................ 604/95 |
| 5,167,221 A * | 12/1992 | Chikama ................ 600/149 |
| 5,269,757 A | 12/1993 | Fagan et al. .............. 604/95 |
| RE34,502 E | 1/1994 | Webster, Jr. .............. 607/125 |
| 5,277,199 A | 1/1994 | DuBois et al. ............ 128/772 |
| 5,281,217 A | 1/1994 | Edwards et al. ........... 606/41 |
| 5,318,525 A | 6/1994 | West et al. ............... 604/95 |
| 5,327,889 A | 7/1994 | Imran ................... 128/642 |

(Continued)

FOREIGN PATENT DOCUMENTS

EP    1 205 208    5/2002

(Continued)

*Primary Examiner*—Nicholas D Lucchesi
*Assistant Examiner*—Scott Medway
(74) *Attorney, Agent, or Firm*—Dykema Gossett PLLC

(57) ABSTRACT

The present invention is a handle for controlling the deflection of a distal end of a catheter body. The catheter body includes first and second deflection wires that extend through the catheter body from the distal end of the catheter body. The handle comprises a slide base, an adjustment knob, a first slide and a second slide. The slide base includes a first end, a second end, and a slide compartment longitudinally extending through at least a portion of the slide base. The adjustment knob is rotateably connected to the first end of the slide base and includes a hole extending through the knob, wherein at least a portion of an inner diameter of the hole includes an internal right thread and an internal left thread. The first slide is located in the slide compartment, is adapted to be coupled to the first deflection wire, and includes an external right thread. The second slide is located in the slide compartment, is adapted to be coupled to the second deflection wire, and includes an external left thread. The internal threads of the knob engage the threads of the slides. Consequently, in operation, rotation of the adjustment knob causes the slides to displace in opposite directions within the slide compartment and the distal end of the catheter body to deflect accordingly.

45 Claims, 22 Drawing Sheets

U.S. PATENT DOCUMENTS

| | | | |
|---|---|---|---|
| 5,327,905 A | 7/1994 | Avitall | 128/772 |
| 5,327,906 A | 7/1994 | Fideler et al. | |
| 5,330,466 A | 7/1994 | Imran | 606/13 |
| 5,342,295 A | 8/1994 | Imran | 604/43 |
| 5,354,297 A | 10/1994 | Avitall | 606/45 |
| 5,359,994 A * | 11/1994 | Krauter et al. | 600/149 |
| 5,364,351 A | 11/1994 | Heinzelman et al. | |
| 5,383,923 A | 1/1995 | Webster, Jr. | 607/125 |
| 5,389,073 A | 2/1995 | Imran | 604/95 |
| 5,391,147 A | 2/1995 | Imran et al. | 604/95 |
| 5,395,327 A * | 3/1995 | Lundquist et al. | 604/528 |
| 5,395,328 A | 3/1995 | Ockuly et al. | 604/95 |
| 5,395,329 A | 3/1995 | Fleischhacker et al. | |
| 5,397,304 A | 3/1995 | Truckai | 604/95 |
| 5,431,168 A | 7/1995 | Webster, Jr. | 128/658 |
| 5,445,148 A | 8/1995 | Jaraczewski et al. | 128/642 |
| 5,478,330 A | 12/1995 | Imran et al. | 604/282 |
| 5,487,385 A | 1/1996 | Avitall | 128/642 |
| 5,487,757 A | 1/1996 | Truckai et al. | 607/122 |
| 5,527,279 A | 6/1996 | Imran | 604/95 |
| 5,533,967 A | 7/1996 | Imran | 604/95 |
| 5,545,200 A | 8/1996 | West et al. | 607/122 |
| 5,549,542 A * | 8/1996 | Kovalcheck | 600/146 |
| 5,562,619 A | 10/1996 | Mirarchi et al. | 604/95 |
| 5,582,609 A | 12/1996 | Swanson et al. | 606/39 |
| 5,588,964 A | 12/1996 | Imran et al. | 604/95 |
| 5,611,777 A | 3/1997 | Bowden et al. | 604/95 |
| 5,626,136 A | 5/1997 | Webster, Jr. | 128/642 |
| 5,656,029 A | 8/1997 | Imran et al. | 604/95 |
| 5,656,030 A | 8/1997 | Hunjan et al. | 604/95 |
| 5,662,606 A * | 9/1997 | Cimino et al. | 604/95.04 |
| 5,755,760 A | 5/1998 | Maguire et al. | 607/122 |
| 5,779,669 A | 7/1998 | Haissaguerre et al. | 604/95 |
| 5,807,249 A | 9/1998 | Qin et al. | 600/374 |
| 5,826,576 A | 10/1998 | West | 128/642 |
| 5,827,272 A | 10/1998 | Breining et al. | 606/41 |
| 5,827,278 A | 10/1998 | Webster | 606/41 |
| 5,836,947 A | 11/1998 | Fleischman et al. | 606/47 |
| 5,842,984 A | 12/1998 | Avitall | 600/374 |
| 5,843,031 A | 12/1998 | Hermann et al. | 604/95 |
| 5,843,076 A | 12/1998 | Webster, Jr. et al. | 606/41 |
| 5,857,997 A * | 1/1999 | Cimino et al. | 604/95.01 |
| 5,861,024 A | 1/1999 | Rashidi et al. | |
| 5,865,800 A | 2/1999 | Mirarchi et al. | 604/95 |
| 5,885,278 A | 3/1999 | Fleischman et al. | 606/43 |
| 5,897,529 A | 4/1999 | Ponzi | 604/95 |
| 5,910,129 A | 6/1999 | Koblish et al. | 604/95 |
| 5,916,213 A | 6/1999 | Haissaguerre et al. | 606/41 |
| 5,916,214 A | 6/1999 | Cosio et al. | 606/41 |
| 5,921,924 A | 7/1999 | Avitall | 600/374 |
| 5,931,811 A | 8/1999 | Haissaguerre et al. | 604/95 |
| 5,935,102 A | 8/1999 | Bowden et al. | 604/95 |
| 5,938,616 A * | 8/1999 | Eaton et al. | 600/463 |
| 5,944,690 A | 8/1999 | Falwell et al. | 604/95 |
| 5,957,943 A * | 9/1999 | Vaitekunas | 606/169 |
| 5,987,344 A | 11/1999 | West | 600/373 |
| 5,993,462 A | 11/1999 | Pomeranz et al. | 606/129 |
| 6,002,955 A | 12/1999 | Willems et al. | 600/374 |
| 6,024,722 A | 2/2000 | Rau et al. | |
| 6,027,473 A | 2/2000 | Ponzi | 604/95 |
| 6,033,403 A | 3/2000 | Tu et al. | 606/41 |
| 6,048,329 A | 4/2000 | Thompson et al. | 604/95 |
| 6,059,739 A | 5/2000 | Baumann | 600/585 |
| 6,064,902 A | 5/2000 | Haissaguerre et al. | 600/381 |
| 6,066,125 A | 5/2000 | Webster, Jr. | 604/528 |
| 6,068,629 A | 5/2000 | Haissaguerre et al. | 606/41 |
| 6,071,274 A | 6/2000 | Thompson et al. | 604/528 |
| 6,071,279 A | 6/2000 | Whayne et al. | 606/41 |
| 6,071,282 A | 6/2000 | Fleischman | 606/41 |
| 6,083,222 A | 7/2000 | Klein et al. | 606/41 |
| 6,090,104 A | 7/2000 | Webster, Jr. | 606/41 |
| 6,123,699 A | 9/2000 | Webster, Jr. | 604/528 |
| 6,138,043 A | 10/2000 | Avitall | 600/377 |
| 6,149,663 A | 11/2000 | Strandberg et al. | 606/180 |
| 6,156,034 A | 12/2000 | Cosio et al. | 606/41 |
| 6,169,916 B1 | 1/2001 | West | 600/373 |
| 6,171,277 B1 | 1/2001 | Ponzi | 604/95.04 |
| 6,178,354 B1 | 1/2001 | Gibson | 607/116 |
| 6,183,435 B1 | 2/2001 | Bumbalough et al. | 604/95.01 |
| 6,183,463 B1 | 2/2001 | Webster, Jr. | 604/528 |
| 6,198,974 B1 | 3/2001 | Webster, Jr. | 607/122 |
| 6,200,315 B1 | 3/2001 | Gaiser et al. | 606/41 |
| 6,203,507 B1 | 3/2001 | Wadsworth et al. | 600/585 |
| 6,203,525 B1 | 3/2001 | Whayne et al. | 604/95.01 |
| 6,210,362 B1 | 4/2001 | Ponzi | 604/95.01 |
| 6,210,407 B1 | 4/2001 | Webster | 606/41 |
| 6,214,002 B1 | 4/2001 | Fleischman et al. | 606/41 |
| 6,221,087 B1 | 4/2001 | Anderson et al. | 606/159 |
| 6,224,587 B1 | 5/2001 | Gibson | 604/528 |
| 6,241,754 B1 | 6/2001 | Swanson et al. | 607/99 |
| 6,308,091 B1 | 10/2001 | Avitall | 600/374 |
| 6,375,654 B1 | 4/2002 | McIntyre | 606/41 |
| 6,430,426 B2 | 8/2002 | Avitall | 600/374 |
| 6,454,758 B1 | 9/2002 | Thompson et al. | 604/528 |
| 6,468,260 B1 * | 10/2002 | Bumbalough et al. | 604/523 |
| 6,485,455 B1 * | 11/2002 | Thompson et al. | 604/95.04 |
| 6,500,167 B1 * | 12/2002 | Webster, Jr. | 604/528 |
| 6,544,215 B1 * | 4/2003 | Bencini et al. | 604/95.01 |
| 6,554,794 B1 * | 4/2003 | Mueller et al. | 604/95.04 |
| 6,582,536 B2 | 6/2003 | Shimda | |
| 6,602,242 B1 * | 8/2003 | Fung et al. | 604/528 |
| 6,652,506 B2 * | 11/2003 | Bowe et al. | 604/523 |
| 6,829,497 B2 * | 12/2004 | Mogul | 600/374 |
| 6,913,594 B2 * | 7/2005 | Coleman et al. | 604/95.04 |
| 7,269,453 B2 * | 9/2007 | Mogul | 600/374 |
| 7,374,553 B2 * | 5/2008 | Koerner et al. | 604/95.04 |
| 7,416,547 B2 * | 8/2008 | Hill et al. | 604/528 |

FOREIGN PATENT DOCUMENTS

| | | |
|---|---|---|
| GB | 1 170 018 | 11/1969 |

* cited by examiner

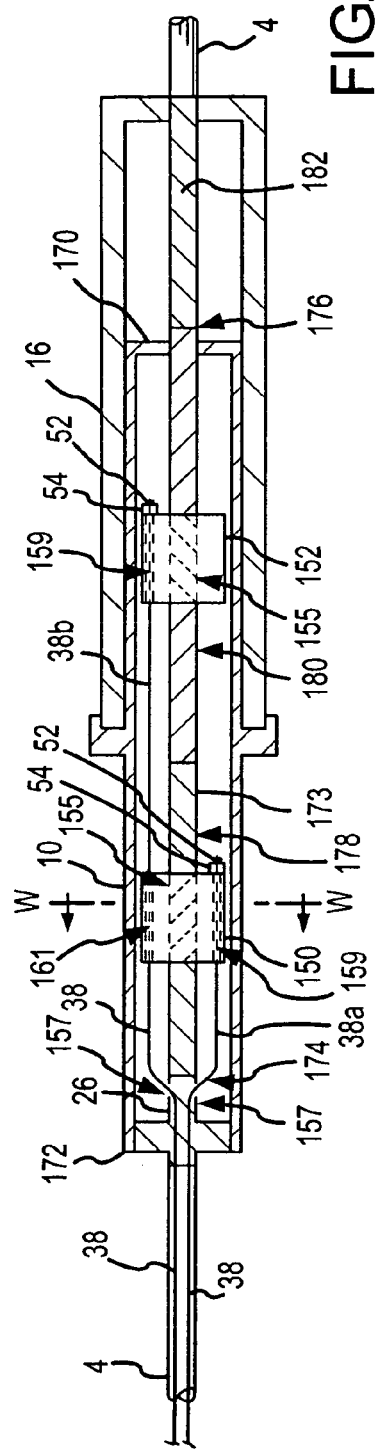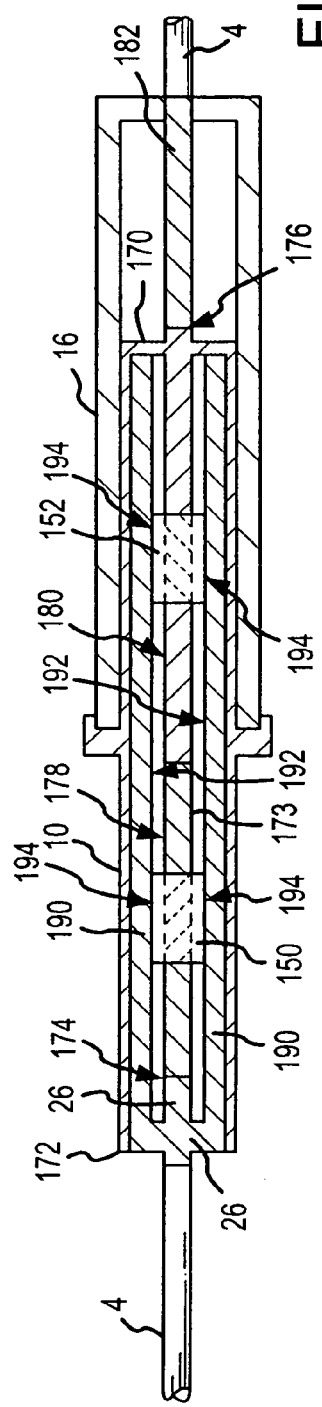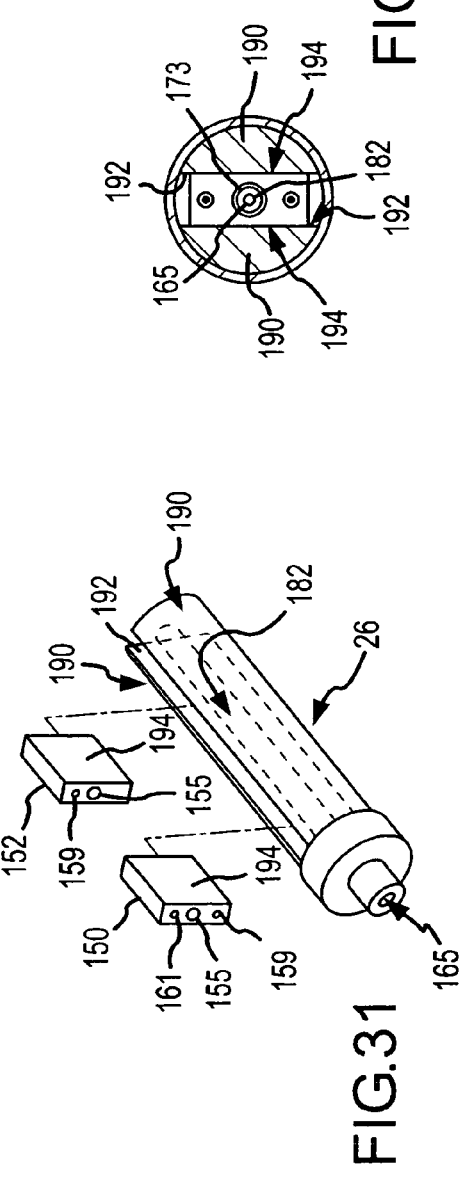

BI-DIRECTIONAL STEERABLE CATHETER CONTROL HANDLE

FIELD OF THE INVENTION

The present invention relates to catheters and sheaths and methods of using catheters and sheaths. More particularly, the present invention relates to control handles for steerable catheters and sheaths and methods of manufacturing and using such handles.

BACKGROUND OF THE INVENTION

Catheters (i.e., catheters or sheaths) that have flexible tubular bodies with deflectable distal ends and control handles for controlling distal end deflection are used for many noninvasive medical procedures. For example, catheters having conductive electrodes along the distal ends of their bodies are commonly used for intra-cardiac electrophysiology studies. The distal end of a catheter body is typically placed into a patient's heart to monitor and/or record the intra-cardiac electrical signals during electrophysiology studies or during intra-cardiac mapping. The orientation or configuration of the distal end is controlled via an actuator located on the catheter's control handle, which remains outside the patient's body. The electrodes conduct cardiac electrical signals to appropriate monitoring and recording devices that are operatively connected at the control handle.

Typically, a catheter body is cylindrical and electrically non-conductive. The catheter body includes a flexible tube constructed from polyurethane, nylon or other electrically non-conductive flexible material. The catheter body further includes braided steel wires or other non-metallic fibers in its wall as reinforcing elements. Each electrode has a relatively fine electrically conductive wire attached thereto and extending through the catheter body. The conductive wire extends from the distal end to a proximal end where electrical connectors such as plugs or jacks are provided to be plugged into a corresponding socket provided in a recording or monitoring device.

The distal portion of the catheter body is selectively deformed into a variety of curved configurations using the actuator on the control handle. The actuator is commonly internally linked to the distal portion of the catheter body by at least one deflection wire. Some catheter bodies employ a single deflection wire, which is pulled (i.e., placed in tension) by the actuator in order to cause the distal portion of the catheter body to deform. Other catheter bodies have at least two deflection wires, where the displacement of one wire (i.e., placing one wire in tension) results in the other wire going slack (i.e., the wire does not carry a compressive load). In such catheters, where the deflection wires are not adapted to carry compressive loads (i.e., the deflection wires are only meant to be placed in tension), the deflection wires are commonly called pull or tension wires.

To deform the distal end of the catheter body into a variety of configurations, a more recent catheter design employs a pair of deflection wires that are adapted such that one of the deflection wires carries a compressive force when the other deflection wire carries a tensile force. In such catheters, where the deflection wires are adapted to carry both compressive and tension loads, the deflection wires are commonly called push/pull or tension/compression wires and the corresponding catheter actuators are called push-pull actuators. U.S. Pat. No. 5,861,024 to Rashidi, which issued Jan. 19, 1999, is representative of a push-pull actuator of this type, and the details thereof are incorporated herein by reference.

Prior art control handles for controlling distal end deflection of catheter bodies have several drawbacks that adversely impact the handles' ability to be operated precisely by a single hand. First, the control handles are often excessively bulky. Second, the control handles are often inadequate with respect to their ability to provide finely controlled deflection adjustment for the distal end of the catheter body. Third, the control handles often provide inadequate deflection wire travel for a desired medical procedure. Fourth, the control handles often have a mechanical advantage that is less than desirable and, as a result, require significant effort to operate on the part of a user. Fifth, once a desired body distal end deflection has been reached, the control handles typically require the physician to take a conscious step to maintain the catheter at the desired deflection. Sixth, the wire displacement mechanisms within the control handles have a tendency to permanently deform the deflection wires. Seventh, the wire displacement mechanisms within the control handles typically make it difficult, if not impossible, to provide a lumen that runs uninterrupted from the proximal end of the control handle to the distal end of the catheter body.

There is a need in the art for a catheter control handle that offers improved single hand operation and deflection adjustment of the distal end of the catheter body. There is also a need in the art for such a handle with a lumen there through. There is also a need in the art for a method of manufacturing and using such a control handle.

BRIEF SUMMARY OF THE INVENTION

The present invention, in one embodiment, is a handle for controlling the deflection of a distal end of a catheter body. The catheter body includes first and second deflection wires that extend through the catheter body from the distal end of the catheter body. Throughout this specification, the term catheter is meant to include, without limitation, catheters, sheaths and similar medical devices.

The handle comprises a slide base, an adjustment knob, a first slide and a second slide. The slide base includes a first end, a second end, and a slide compartment longitudinally extending through at least a portion of the slide base. The adjustment knob is rotateably connected to the first end of the slide base and includes a hole extending through the knob, wherein at least a portion of an inner diameter of the hole includes an internal right thread and an internal left thread. The first slide is located in the slide compartment, is adapted to be coupled to the first deflection wire, and includes an external right thread. The second slide is located in the slide compartment, is adapted to be coupled to the second deflection wire, and includes an external left thread. The internal threads of the knob engage the external threads of the slides. Consequently, in operation, rotation of the adjustment knob causes the slides to displace in opposite directions within the slide compartment and the distal end of the catheter body to deflect accordingly.

The present invention, in another embodiment, is a handle for controlling the deflection of a distal end of a catheter body, wherein the catheter body includes a first deflection wire and a second deflection wire. The handle comprises a first handle portion, a second handle portion, a first member and a second member. The first handle portion is rotateably coupled to the second handle portion. The first member and the second member are longitudinally displaceable within the handle. The first member is adapted to couple to the first deflection wire, and the second member is adapted to couple to the second deflection wire. Rotation of the first handle portion relative to the second handle portion causes the members to displace in opposite directions.

In one embodiment, the displacement of the members is along a longitudinal axis of the handle. Also, the rotation of the first handle portion is about a longitudinal axis of the second handle portion.

In one embodiment, rotational movement of the first handle portion is transmitted into linear movement of the members via a threaded arrangement. For example, in one embodiment, the threaded arrangement includes a first right thread along an outer circumferential surface of the first member, a first left thread along an outer circumferential surface of the second member, and a second right thread and a second left thread along an inner circumferential surface of the first handle portion. The left threads engage each other and the right threads engage each other.

In another embodiment, the threaded arrangement includes a first right thread along an inner circumferential surface of the first member, a first left thread along an inner circumferential surface of the second member, and a second right thread and a second left thread along an outer circumferential surface of the first handle portion. The left threads engage each other and the right threads engage each other.

In one embodiment, where the first and second members have external threads and the first handle portion has inner threads, the second right thread is located in a proximal portion of the first handle portion, the second left thread is located in a distal portion of the first handle portion, and the first and second members are positioned relative to each other within the first handle portion in a generally end-to-end arrangement. In a similar embodiment, the thread locations are reversed such that the second right thread is located in a distal portion of the first handle portion and the second left thread is located in a proximal portion of the first handle portion.

In another embodiment, the second right thread and the second left thread are located generally at the same location within the first handle portion such that the second left thread and the second right thread form a bi-directional threading configuration along the inner circumferential surface of the first handle portion. Thus, in such an embodiment, the first and second members may be positioned relative to each other within the first handle portion in a generally side-by-side arrangement. Each member has a generally planar side face that slideably abuts against the generally planar side face of the other member as the members displace oppositely relative to each other. Also, each member has a distal portion that carries the member's respective thread and a proximal portion that has a generally planar face for slideably abutting against a generally planar portion of a slot in the second handle portion. Alternatively, each member has a distal portion that carries the member's respective thread and a proximal portion that has a first feature for slideably abutting against a second feature in a cavity within the second handle portion. This prevents the members from rotationally displacing within the cavity when the first handle portion is rotated relative to the second handle portion.

In one embodiment, the members displace along an outer surface of the catheter body. Similarly, in one embodiment, the handle includes a wire guide extending through at least a portion of the first handle portion, and the members are displaceable along an outer surface of the wire guide. In one such embodiment, the wire guide has a non-circular latitudinal cross-section, which, in one embodiment, is generally rectangular.

In one embodiment, where the wire guide has a generally circular latitudinal cross-section, the wire guide has a first feature for engaging a second feature of the first member, thereby preventing the rotational displacement of the first member about the wire guide. In one embodiment, the first feature is a groove and the second feature is a key for being slideably received in the groove.

In one embodiment, the first handle portion includes a cavity and a threaded shaft extending through the cavity and along a longitudinal axis of the first handle portion. In one such embodiment, the threaded shaft includes a first outer circumferential portion with right hand threads and a second outer circumferential portion with left hand threads. Also, the first member and the second member each include a hole whereby the threaded shaft may pass through each member. The hole of the first member includes a right hand thread on an inner circumferential surface of said hole for engaging the right hand threads of the threaded shaft. Similarly, the hole of the second member includes a left hand thread on an inner circumferential surface of said hole for engaging the left hand threads of the threaded shaft.

In one embodiment utilizing the threaded shaft, the handle further comprises a wire guide including a feature adapted to prevent the members from rotationally displacing about the threaded shaft when the first handle portion is rotated relative to the second handle portion. In one embodiment, the feature is a generally planar portion extending longitudinally along the cavity and against which a generally planar portion of each member may slideably displace.

In one embodiment, each member includes a coupling arrangement between the member and its respective deflection wire that allows deflection wire tension to be adjusted prior to displacing the member. In one embodiment, a coupling arrangement between each member and its respective deflection wire allows a member to displace relative to its respective deflection wire when the member is displaced distally, but requires the wire to displace with the member when the member is displacing proximally.

The present invention, in one embodiment, is a method of deflecting a distal end of a catheter body, wherein the catheter body includes first and second deflection wires. The method comprises coupling a first member to the first deflection wire, coupling a second member to the second deflection wire, and rotateably coupling a first handle portion to a second handle portion. The first member includes a right thread, and the second member includes a left thread. The first handle portion includes a right thread and a left thread and said threads are engaged with the threads of the first and second members. The method further comprises rotating the first handle portion relative to a second handle portion such that the members are caused to displace in opposite directions and the distal end of the catheter body is deflected.

The present invention, in one embodiment, is a surgical method. When performing the surgical method, one provides a catheter including a catheter body and a control handle attached to a proximal end of the catheter body. In one embodiment, the handle includes an adjustment knob rotateably coupled to a base. The distal end of the catheter body is first inserted into a patient (e.g., intravenously, percutaneously, or via other avenues of entering the patient). The distal end is then advanced until positioned in a selected location within the patient (e.g., within a chamber of the patient's heart or other organ, within a body cavity of the patient, etc.). The distal end is then deflected by rotating the adjustment knob about a longitudinal axis of the base. This causes a pair of members in the handle to oppositely displace along the longitudinal axis. Since each member is coupled to a deflection wire running though the catheter body, and each deflection wire is coupled to the distal end of the catheter body, the distal end of the catheter body deflects.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 29 is a longitudinal sectional elevation of another embodiment of the handle taken along section line YY of FIG. 23.

FIG. 30 is a longitudinal sectional plan view of the handle depicted in FIG. 29 taken along section line VV in FIG. 23 and wherein section line VV forms a plane that is perpendicular to the plane formed by section line YY in FIG. 23.

FIG. 31 is an isometric view of one embodiment of the wire guide.

FIG. 32 is a latitudinal sectional elevation of the handle as taken along section line WW in FIG. 29.

DETAILED DESCRIPTION

Figure 1:
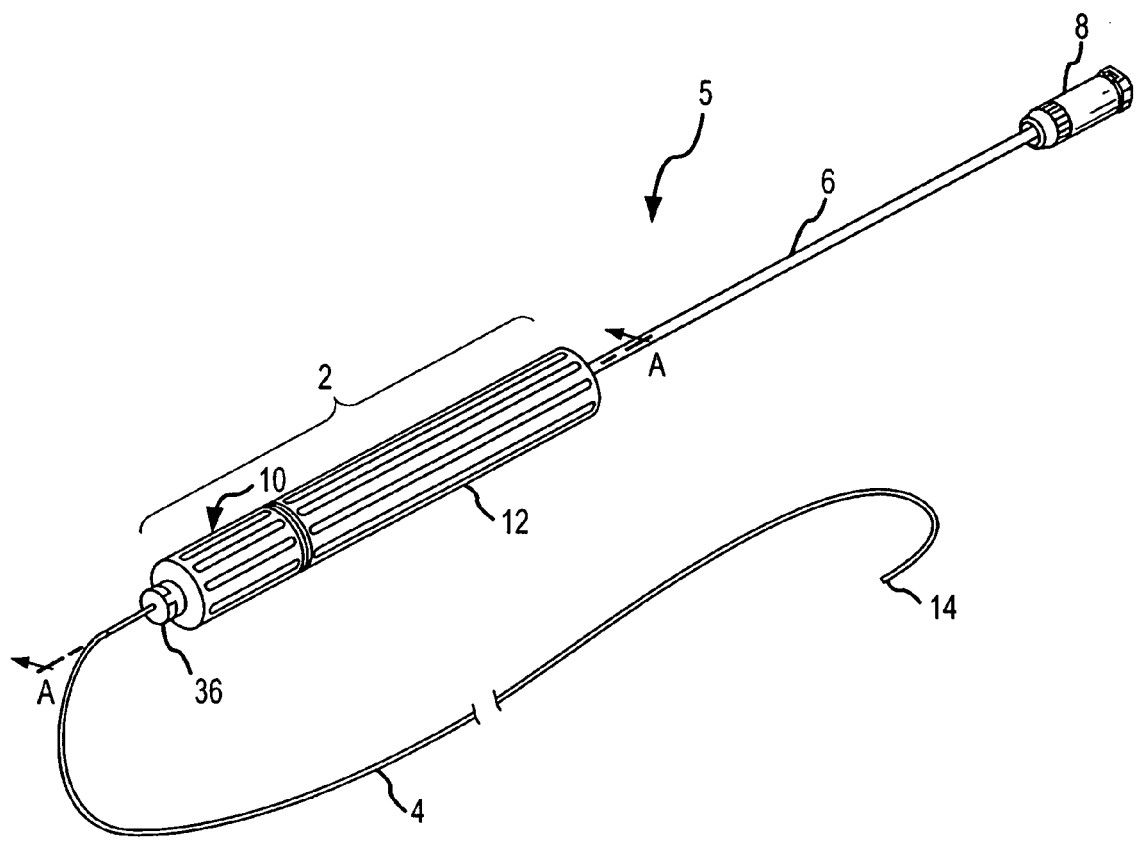
FIG. 1 is an isometric view of one embodiment of the present invention, which is a control handle for a catheter or sheath.

FIG. 1 is an isometric view of one embodiment of the present invention, which is a control handle 2 for a flexible tubular body 4 of a catheter 5. Throughout this specification, the term catheter is meant to include, without limitation, catheters, sheaths and similar medical devices. As shown in FIG. 1, in one embodiment, the distal end of the handle 2 is connected to the catheter body 4 and the proximal end of the handle 2 is connected to tubing 6 that contains electrical wire and extends to an electrical connector 8. The handle 2 includes an adjusting knob 10 and a handle grip 12. As will become clear from this specification, the handle 2 of the present invention is advantageous in that it is compact and allows a user to manipulate the catheter body's extreme distal end 14 in a bi-directional manner by pivoting the adjusting knob 10 relative to the handle grip 12 in one direction or the other about the longitudinal axis of the handle 2. Furthermore, in one embodiment, the handle 2 has a lumen that runs uninterrupted from the proximal end of the handle 2 to the extreme distal end 14 of the catheter body 4. This lumen can be used to provide contrast injection for guide wire insertion.

Figure 2:
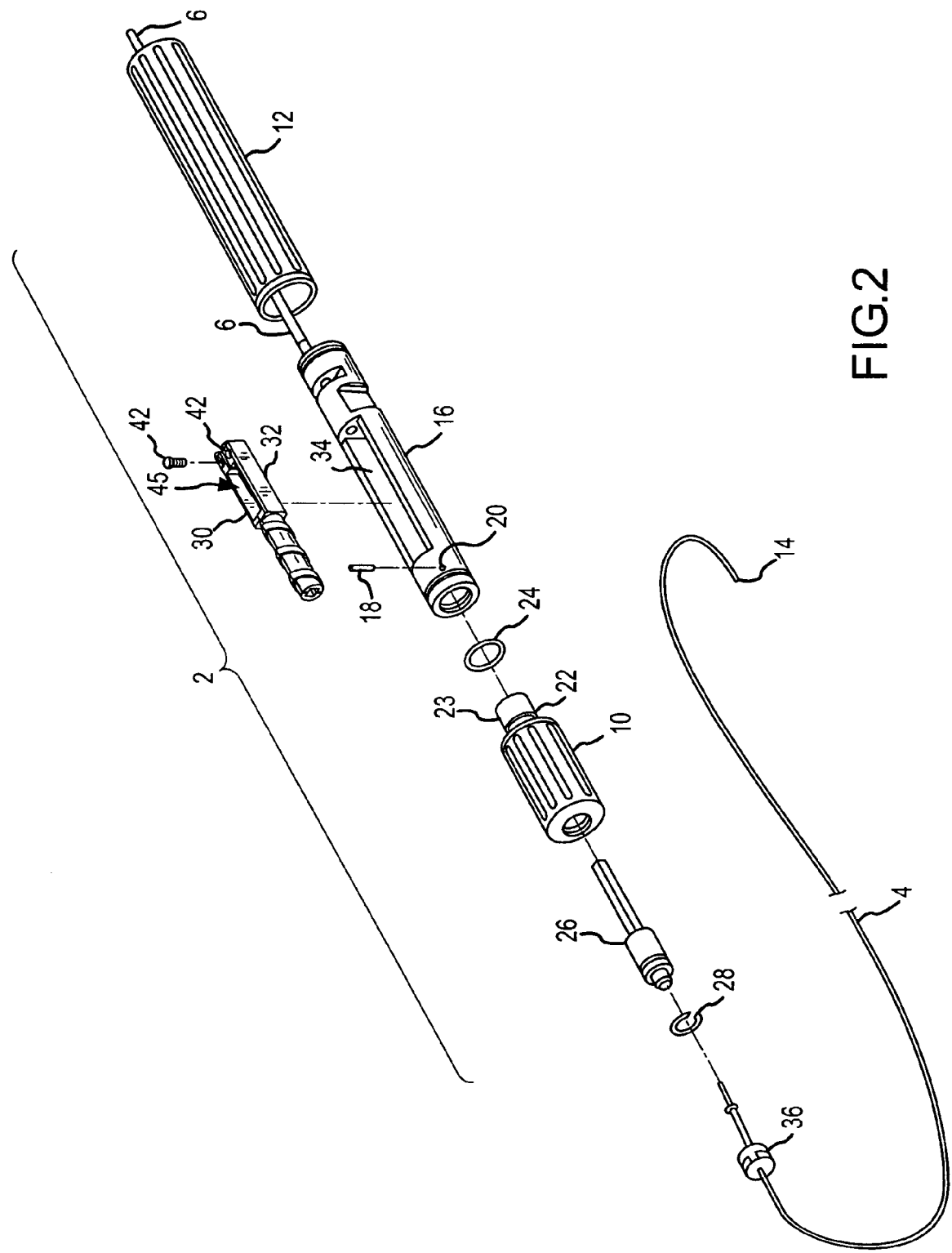
FIG. 2 is an isometric view of the handle exploded to show its various components.
Figure 3:
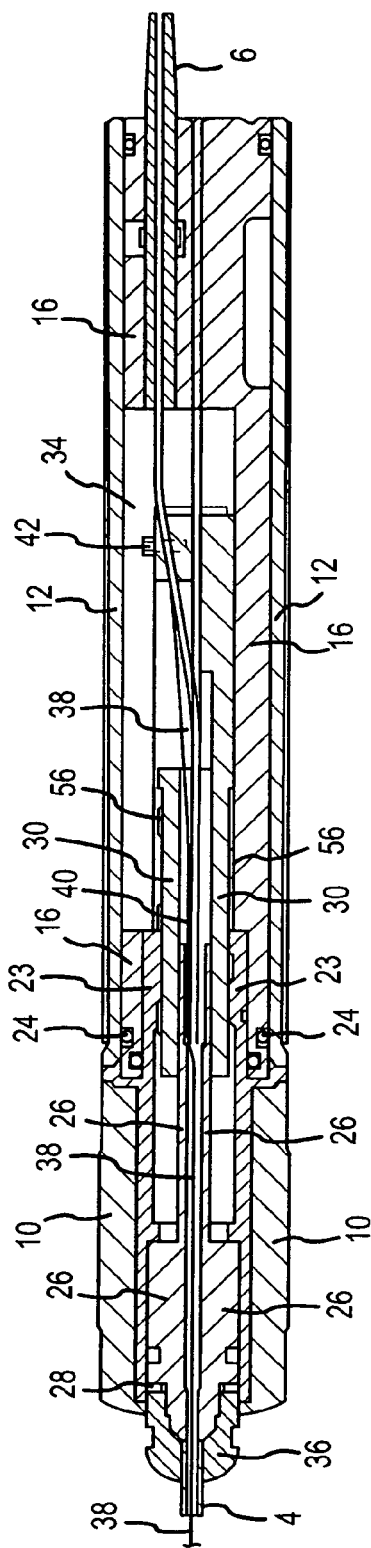
FIG. 3 is a longitudinal sectional elevation of the handle taken along section line AA of FIG. 1.

For a more detailed discussion of the handle 2, reference is now made to FIGS. 2 and 3. FIG. 2 is an isometric view of the handle 2 exploded to show its various components. FIG. 3 is a longitudinal sectional elevation of the handle 2 taken along section line AA of FIG. 1.

As shown in FIGS. 2 and 3, the adjusting knob 10 is pivotally attached to a mounting shaft (i.e., a slide base or base portion) 16 contained within the handle grip 12. To pivotally attach the knob 10 to the mounting shaft 16, a dowel pin 18 is inserted into a pinhole 20 in the distal end of the shaft 16 and mates with a groove 22 in a hub portion 23 of the knob 10. A silicone o-ring 24 exists between the hub portion 23 of the knob 10 and the distal end of the shaft 16.

As indicated in FIGS. 2 and 3, a wire guide 26 is positioned within the adjusting knob 10 and is held in place by a retaining ring 28. A right slide or member 30 and a left slide or member 32 are slideably positioned within a slot (i.e., a slide compartment) 34 in the mounting shaft 16. A catheter body-retaining nut 36 is used to secure the catheter body 4 to the distal end of the wire guide 26.

As illustrated in FIG. 3, a pair of deflection wires 38 extend from the extreme distal end 14 of the body 4, through the body 4, the wire guide 26 and a passage 40 formed between the two slides 30, 32, to a point near a proximal portion of the slides 30, 32. Each wire 38 then affixes to an individual slide 30, 32 via a retention screw 42.

Figure 4:
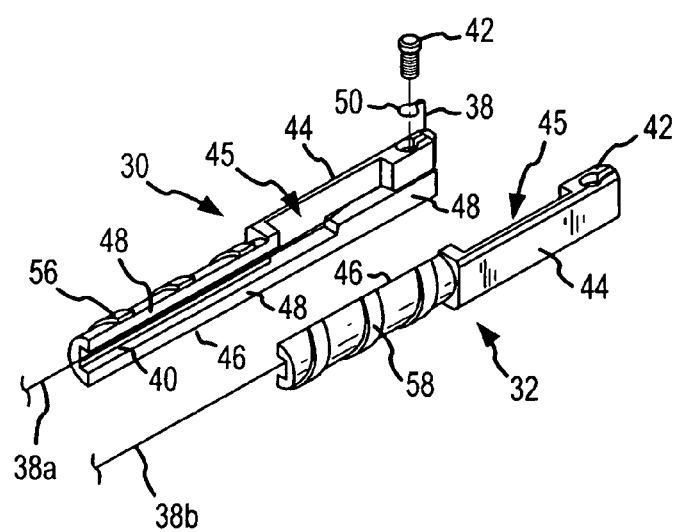
FIG. 4 is an isometric view of the right and left slides with their respective deflection wires attached.

For a more detailed discussion of the slides 30, 32 and their relationship to the deflection wires 38, reference is now made to FIG. 4, which is an isometric view of the deflection wires 38a, 38b attached to the right and left slides 30, 32. As shown in FIG. 4, the slides 30, 32, which are mirror images of each other, each have a rectangular box-like proximal portion 44 and a half-cylinder distal portion 46. Each proximal portion 44 has a generally planar outer sidewall and bottom wall. These planar surfaces slideably displace against the generally planar sides and bottom of the slot 34, which act as thrust surfaces for the slides 30, 32.

Each half-cylinder distal portion 46 is hollowed out along its longitudinal axis to form the passage 40 through which the deflection wires 38a, 38b and, as indicated in FIG. 3, the narrow proximal portion of the wire guide 26 extend when the slides 30, 32 are in the assembled handle 2. Each slide 30, 32 has a planar slide face 48 that is meant to slideably abut against the planar slide face 48 of the opposing slide 30, 32. Thus, as illustrated in FIG. 2, when the planar slide faces 48 of the slides 30, 32 abut against each other and the extreme proximal ends of each slide 30, 32 are flush with each other, the half-cylinder distal portions 46 of each slide 30, 32 combine to form a complete cylinder with a channel or passage 40 there through.

Figure 5:
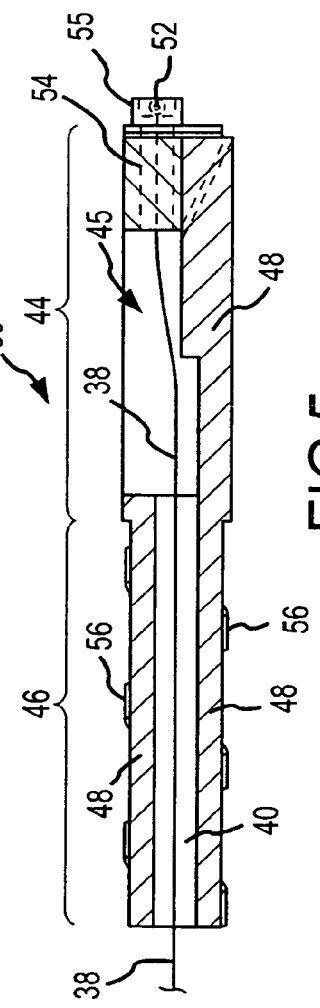
FIG. 5 is a side elevation of an exemplary slide illustrating a means of securing a deflection wire to the proximal end of the slide.

As shown in FIG. 4, in one embodiment, the proximal end of each deflection wire 38a, 38b forms a loop 50 through which a retention screw 42 passes to secure the wire 38a, 38b to the proximal portion of the respective slide 30, 32. As indicated in FIG. 5, which is a side elevation of an exemplary slide 30, in one embodiment, the proximal end of each deflection wire 38 forms a knot 52. The wire 38 passes through a hollow tension adjustment screw 54 and the knot 52 abuts against the head 55 of the screw 54, thereby preventing the wire 38 from being pulled back through the screw 54. In one embodiment, the screw's longitudinal axis and the longitudinal axis of the slide 30, 32 are generally parallel. Each tension adjustment screw 54 is threadably received in the proximal end of its respective slide 30, 32. Tension in a wire 38 may be increased by outwardly threading the wire's tension adjustment screw 54. Conversely, tension in a wire 38 may be decreased by inwardly threading the wire's tension adjustment screw 54.

As can be understood from FIG. 4, in one embodiment where the wires 38a, 38b are intended to only transmit tension forces, the wires 38a, 38b may deflect or flex within an open area 45 defined in the proximal portion 44 of each slide 30, 32 when the slides 30, 32 displace distally. Similarly, as can be understood from FIG. 5, in another embodiment where the wires 38 are intended to only transmit tension forces, the wires 38 may slide proximally relative to the screw 54 when the slides 30, 32 displace distally.

As shown in FIG. 4, in one embodiment, the outer circumference of the half-cylinder distal portion 46 of the right slide 30 is threaded with a right-hand thread 56, and the outer circumference of the half-cylinder distal portion 46 of the left slide 32 is threaded with a left-hand thread 58. In one embodiment, the outer circumference of the half-cylinder distal portion 46 of the right slide 30 is threaded with a left-hand thread, and the outer circumference of the half-cylinder distal portion 46 of the left slide 32 is threaded with a right-hand thread.

Figure 6:
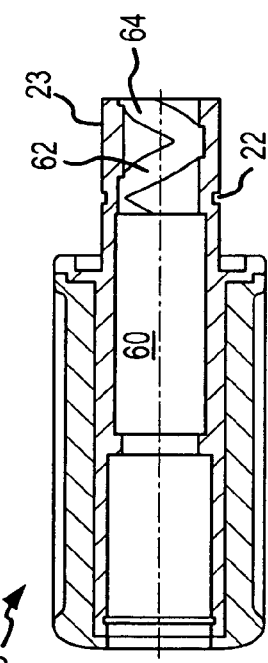
FIG. 6 is a longitudinal sectional elevation of the adjusting knob taken along section line AA of FIG. 1.

For a better understanding of the relationship of the slide threads 56, 58 to the rest of the handle 2, reference is now made to FIG. 6, which is a longitudinal sectional elevation of the adjusting knob 10 taken along section line AA of FIG. 1. As indicated in FIG. 6, a cylindrical hole or shaft 60 passes through the knob 10 along the knob's longitudinal axis. In the hub portion 23 of the knob 10, the inner circumferential surface of the shaft 60 has both right hand threads 62 and left hand threads 64. These internal threads 62, 64 of the knob 10 mate with the corresponding external threads 56, 58 of the slides 30, 32. More specifically, the right internal threads 62 of the knob 10 mate with the right external threads 56 of the right slide 30, and the left internal threads 64 of the knob 10 mate with the left external threads 58 of the left slide 32.

Thus, as can be understood from FIGS. 2, 3, 4 and 6, in one embodiment, as the knob 10 is rotated clockwise relative to the longitudinal axis of the handle 2, the internal and external right threads 62, 56 engage and the internal and external left threads 64, 58 engage, thereby causing simultaneous opposed displacement of the right and left slides 30, 32 longitudinally within the slot 34 in the handle 10. Specifically, because of the threading arrangement of the knob 10 and the slides, 30, 32, the right slide 30 moves distally within the slot 34 and the left slide 32 moves proximally within the slot 34 when the knob 10 is rotated clockwise relative to the handle grip 12 of the handle 2. Conversely, when the knob 10 is rotated in a counterclockwise manner relative to the handle grip 12 of the handle 2, the right slide 30 moves proximally within the slot 34 and the left slide 32 moves distally within the slot 34.

As can be understood from FIGS. 4 and 6, when the knob 10 is rotated such that the right slide 30 is urged distally and the left slide 32 is urged proximally, the deflection wire 38a connected to the right slide 30 is placed into compression and the deflection wire 38b connected to the left slide 32 is placed into tension. This causes the extreme distal end 14 of the catheter body 4 to deflect in a first direction. Conversely, when the knob 10 is rotated such that the right slide 30 is urged proximally and the left slide 32 is urged distally, the deflection wire 38a connected to the right slide 30 is placed into tension and the deflection wire 38b connected to the left slide 32 is placed into compression. This causes the extreme distal end 14 of the catheter body 4 to deflect in a second direction that is opposite the first direction.

The control handle 2 of the present invention as described has several advantages. First, the handle 2 is compact and may be operated with a single hand. Second, the threaded slides 30, 32 and knob 10 allow a physician to make fine, controlled adjustments to the bend in the distal end 14 of the catheter body 4. Third, once the knob 10 is rotated so as to cause a bend in the distal end 14 of the catheter body 4, the threads 56, 58, 62, 64 interact to maintain the bend without requiring any action on the physician's part. Fourth, because the slides 30, 32 simply displace distally and proximally along the longitudinal axis of the handle 2, they are less likely to permanently deform the wires 38 as compared to the wire displacement mechanisms in some prior art handles. Fifth, the threads 56, 58, 62, 64 are mechanically advantageous in that they provide increased deflection wire travel and reduced actuation effort for the physician, as compared to some prior art handles.

Figure 33:
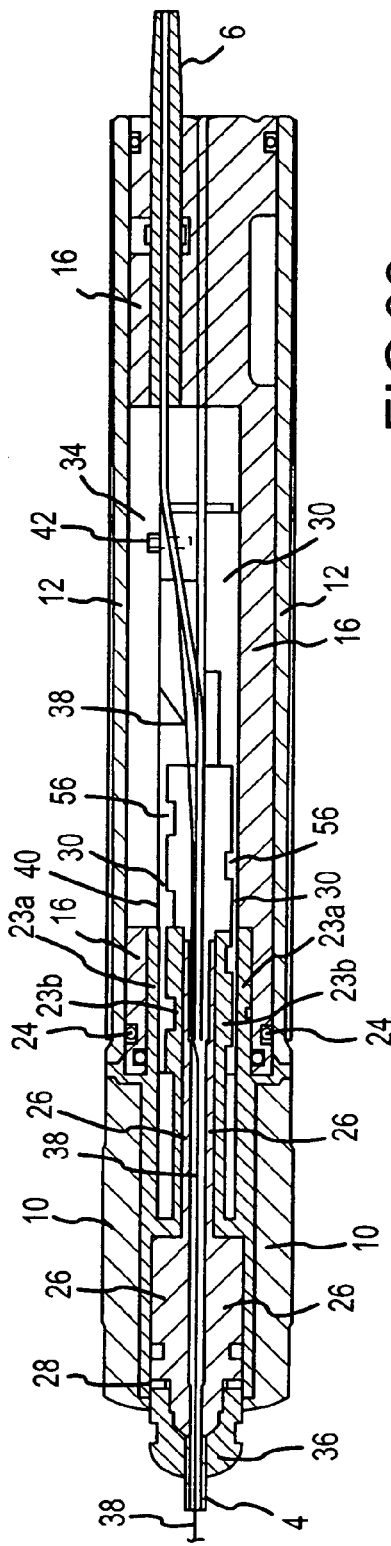
FIG. 33 is a longitudinal sectional elevation of the handle taken along section line AA of FIG. 1.
Figure 34:
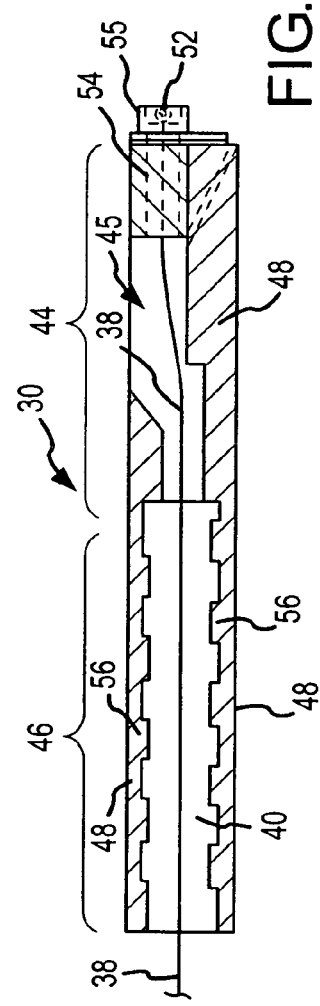
FIG. 34 is a side elevation of an exemplary slide employed in the embodiment depicted in FIG. 33.
Figure 35:
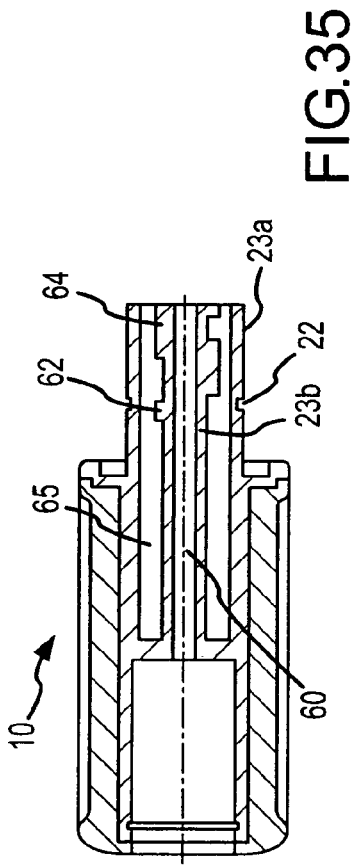
FIG. 35 is a longitudinal sectional elevation of the adjusting knob taken along section line AA of FIG. 1.

While FIGS. 2-6 depict an embodiment where the slides 30, 32 have external threads 56, 58 and the knob 10 has internal threads 62, 64, in other embodiments the threading arrangement is reversed. For a discussion of one such embodiment, reference is made to FIGS. 33-35. FIG. 33 is a longitudinal sectional elevation of the handle 2 taken along section line AA of FIG. 1. FIG. 34 is a side elevation of an exemplary slide employed in the embodiment depicted in FIG. 33. FIG. 35 is a longitudinal sectional elevation of the adjusting knob taken along section line AA of FIG. 1.

A comparison of the embodiment depicted in FIGS. 33-35 to the embodiment depicted in FIGS. 3, 5 and 6 reveals that the two embodiments are generally the same, except as will be described in the following discussion of FIGS. 33-35. Reference numbers utilized in FIGS. 33-35 pertain to the same or similar features identified by the same reference numbers in FIGS. 3, 5 and 6.

As shown in FIG. 33, the adjusting knob 10 is pivotally attached to a mounting shaft (i.e., a slide base or base portion) 16 contained within the handle grip 12. A wire guide 26 is positioned within the adjusting knob 10. Like the embodiment depicted in FIG. 2, the embodiment illustrated in FIG. 33 includes a right slide or member 30 and a left slide or member 32 that are slideably positioned within a slot (i.e., a slide compartment) 34 in the mounting shaft 16.

As can be understood from FIG. 34, the slides 30, 32, which are mirror images of each other, each have a rectangular box-like proximal portion 44 and a distal portion 46 that may be rectangular or half-cylindrical. Each proximal portion 44 has a generally planar outer sidewall and bottom wall. These planar surfaces slideably displace against the generally planar sides and bottom of the slot 34, which act as thrust surfaces for the slides 30, 32.

Each distal portion 46 is hollowed out to form half of a cylindrical passage 40 that is created when the slides 30, 32 are abutted against each other in a side-by-side relationship. Thus, each distal portion 46 of each slide 30, 32 includes an inner circumferential surface, which when combined with the inner circumferential surface of the other slide 30, 32, defines the cylindrical passage 40.

As indicated in FIG. 34, in one embodiment, the inner circumferential surface of the right slide 30 is threaded with a right-hand thread 56. Similarly, as can be understood from FIG. 34, the inner circumferential surface of the left slide 32 is threaded with a left-hand thread 58. Thus, the distal portion 46 of each slide 30, 32 is equipped with internal threads. In another embodiment, the inner circumferential surface of the right slide 30 is threaded with a left-hand thread 58. Similarly, the inner circumferential surface of the left slide 32 is threaded with a right-hand thread 56.

As indicated in FIG. 35, the knob 10 includes an outer hub 23a surrounding an inner hub 23b. A space 65 exists between, and is defined by, the inner and outer hubs 23a, 23b. The space 65 is adapted to receive the distal ends 46 of each slide 30, 32. The outer circumferential surface of the inner hub 23b has both right hand threads 62 and left hand threads 64. These external threads 62, 64 of the knob 10 mate with the corresponding internal threads 56, 58 of the slides 30, 32. More specifically, the right external threads 62 of the knob 10 mate with the right internal threads 56 of the right slide 30, and the left external threads 64 of the knob 10 mate with the left internal threads 58 of the left slide 32.

As can be understood from FIG. 33, in one embodiment, as the knob 10 is rotated clockwise relative to the longitudinal axis of the handle 2, the internal and external right threads 56, 62 engage and the internal and external left threads 58, 64 engage, thereby causing simultaneous opposed displacement of the right and left slides 30, 32 longitudinally within the slot 34 in the handle 10. Specifically, because of the threading arrangement of the knob 10 and the slides, 30, 32, the right slide 30 moves distally within the slot 34 and the left slide 32 moves proximally within the slot 34 when the knob 10 is rotated clockwise relative to the handle grip 12 of the handle 2. Conversely, when the knob 10 is rotated in a counterclockwise manner relative to the handle grip 12 of the handle 2, the right slide 30 moves proximally within the slot 34 and the left slide 32 moves distally within the slot 34.

As can be understood from FIG. 33, when the knob 10 is rotated such that the right slide 30 is urged distally and the left slide 32 is urged proximally, the deflection wire 38 connected to the right slide 30 is placed into compression and the deflection wire 38 connected to the left slide 32 is placed into tension. This causes the extreme distal end 14 of the catheter body 4 to deflect in a first direction. Conversely, when the knob 10 is rotated such that the right slide 30 is urged proximally and the left slide 32 is urged distally, the deflection wire 38 connected to the right slide 30 is placed into tension and the deflection wire 38 connected to the left slide 32 is placed into compression. This causes the extreme distal end 14 of the catheter body 4 to deflect in a second direction that is opposite the first direction.

Figure 7:
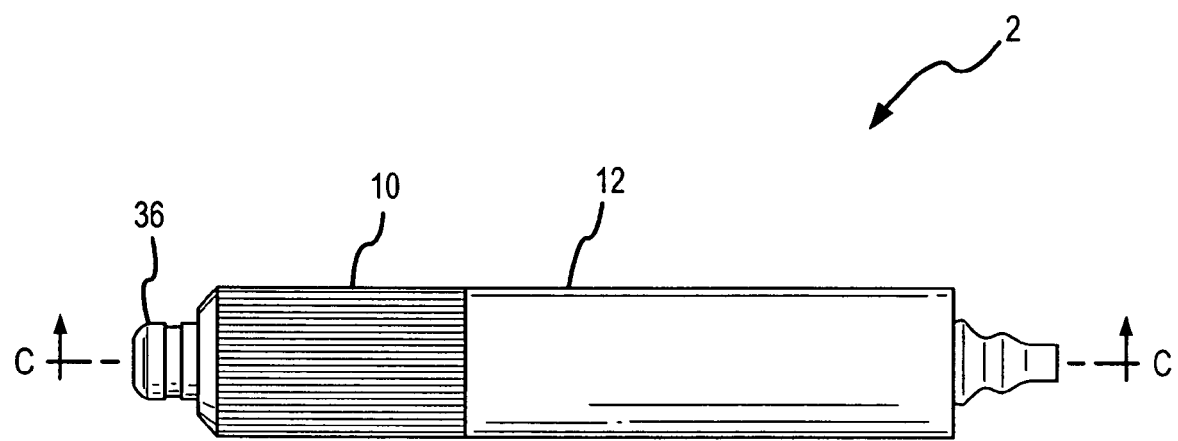
FIG. 7 is a plan view of another embodiment of the handle.
Figure 8:
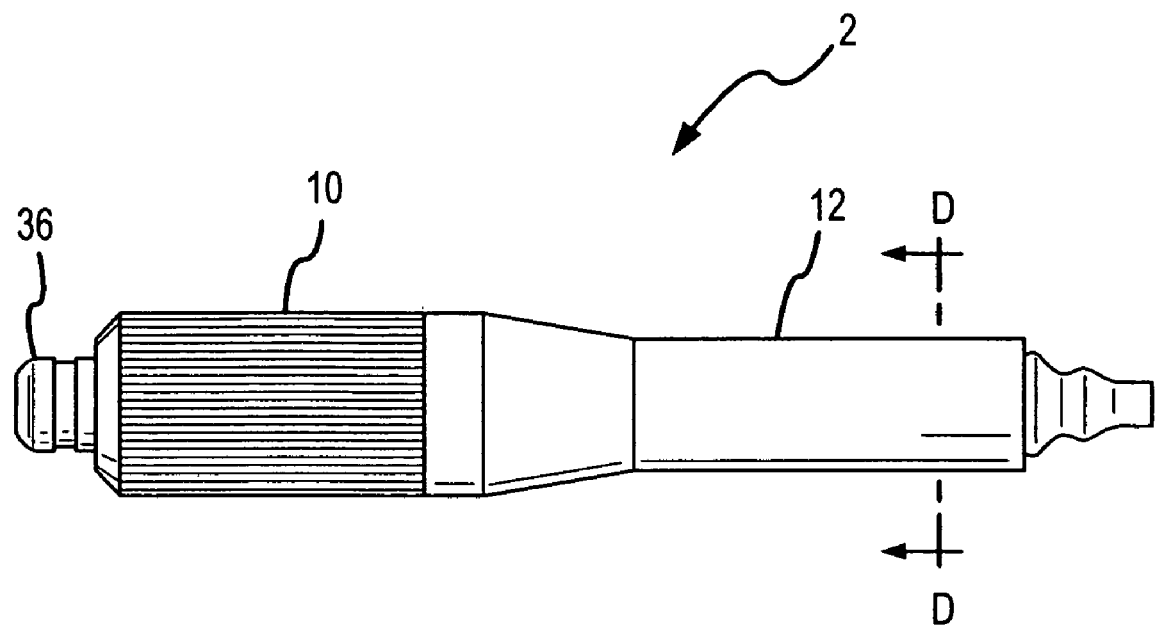
FIG. 8 is a side elevation of the handle depicted in FIG. 7.
Figure 9:
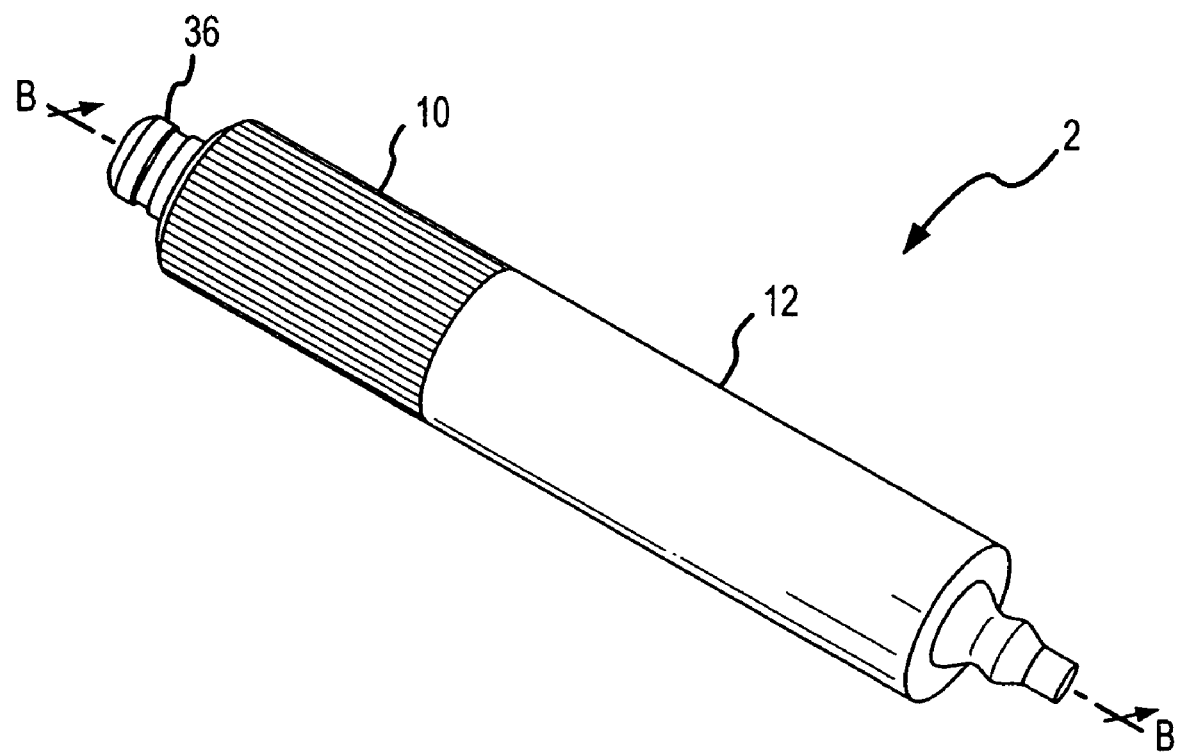
FIG. 9 is an isometric view of the distal end of the handle depicted in FIG. 7.

For a detailed discussion of another embodiment of the handle 2 of the present invention, reference is now made to FIGS. 7, 8 and 9. FIG. 7 is a plan view of the handle 2. FIG. 8 is a side elevation of the handle 2. FIG. 9 is an isometric view of the distal end of the handle 2.

As shown in FIGS. 7-9, the handle 2 includes an adjusting knob 10 on its distal end and a handle grip 12 on its proximal end. As can be understood from FIGS. 7-9, in one embodiment, the knob 10 has a generally circular cross-section and the handle grip 12 has a generally oval cross-section. In one embodiment, both the knob 10 and the handle grip 12 have generally circular cross-sections. The oval cross-section of the handle grip 12 is advantageous because it provides the physician with a tactile indication of the catheter's rotational position.

Figure 10:
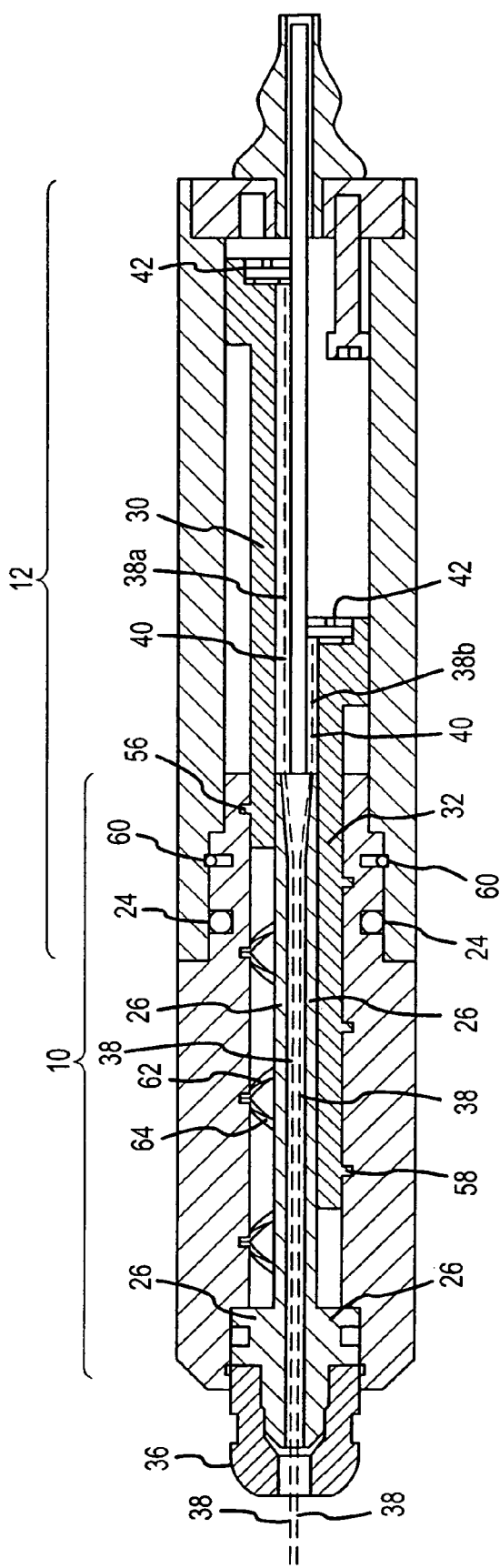
FIG. 10 is a longitudinal sectional plan view of the handle taken along section line BB of FIG. 9.

For a more detailed discussion of the components of the handle 2, reference is now made to FIG. 10, which is a longitudinal sectional plan view of the handle 2 taken along section line BB of FIG. 9. As shown in FIG. 10, an o-ring 24 is located between the handle grip 12 and a groove in the knob 10. The knob 10 is pivotally affixed to the handle grip 12 via a rotating retaining-ring 60 that resides within grooves in both the knob and the handle grip 12.

Figure 11:
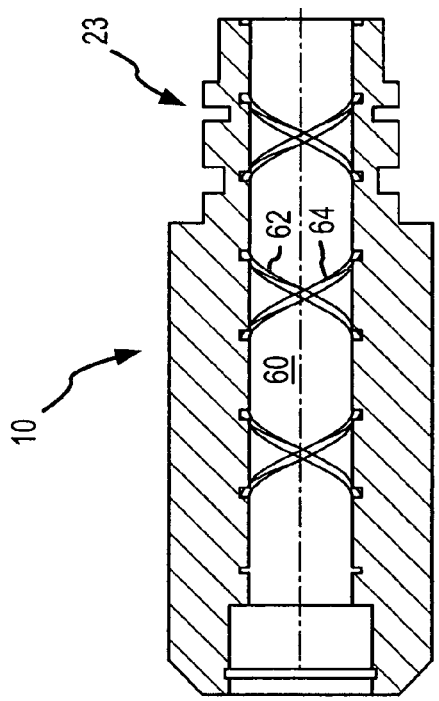
FIG. 11 is a longitudinal sectional plan view of the knob taken along section line BB in FIG. 9.

As illustrated in FIG. 10, a catheter body-retaining nut 36 is threadably affixed to the distal end of a wire guide 26 that extends along the axial center of the knob 10. As indicated in FIG. 10 and more clearly shown in FIG. 11, which is a longitudinal sectional plan view of the knob 10 taken along section line BB in FIG. 9, a cylindrical hole or shaft 60 passes through the knob 10 along the knob's longitudinal axis. The inner circumferential surface of the shaft 60 has both right hand threads 62 and left hand threads 64 that extend towards the distal end of the knob 10 from a hub portion 23 of the knob 10. As shown in FIG. 11, in one embodiment, the knob 10 is a singular integral piece.

Figure 12:
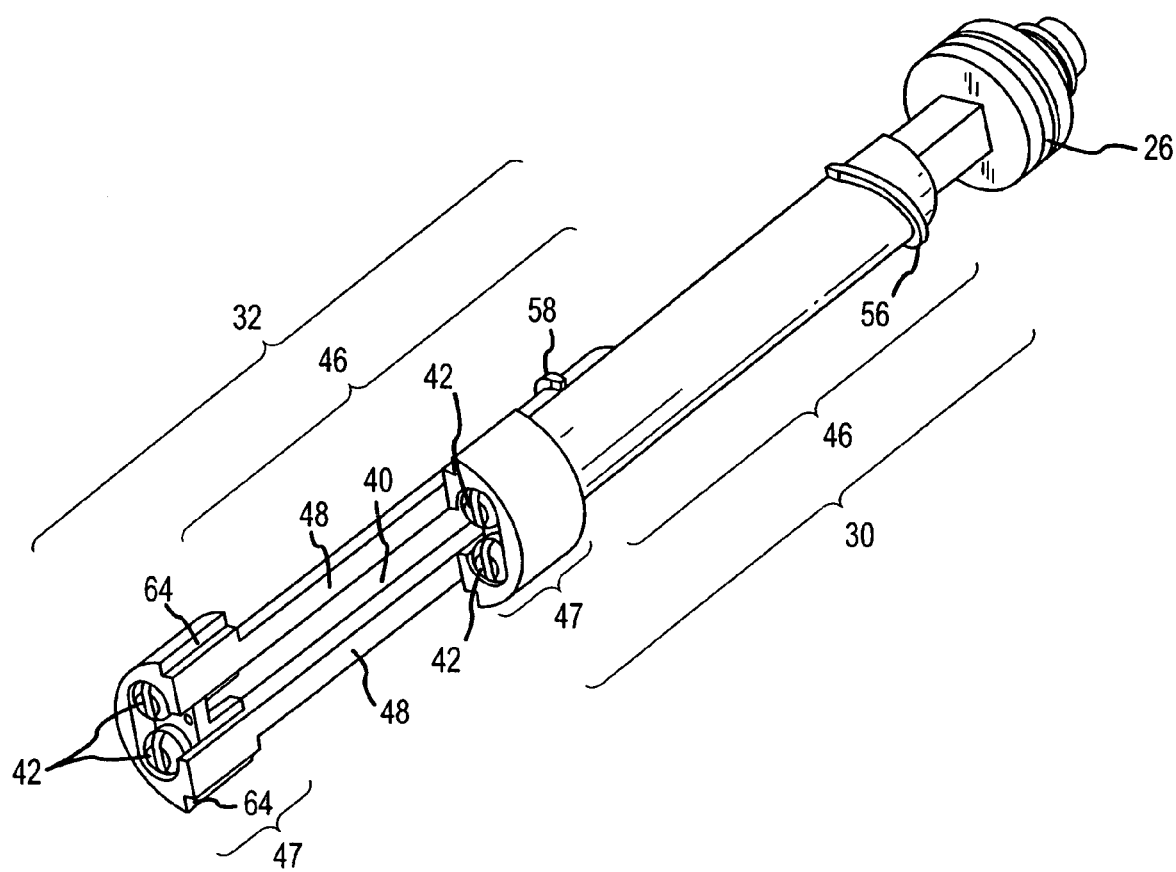
FIG. 12 is a right side isometric view of the slides displaced about the wire guide.
Figure 13:
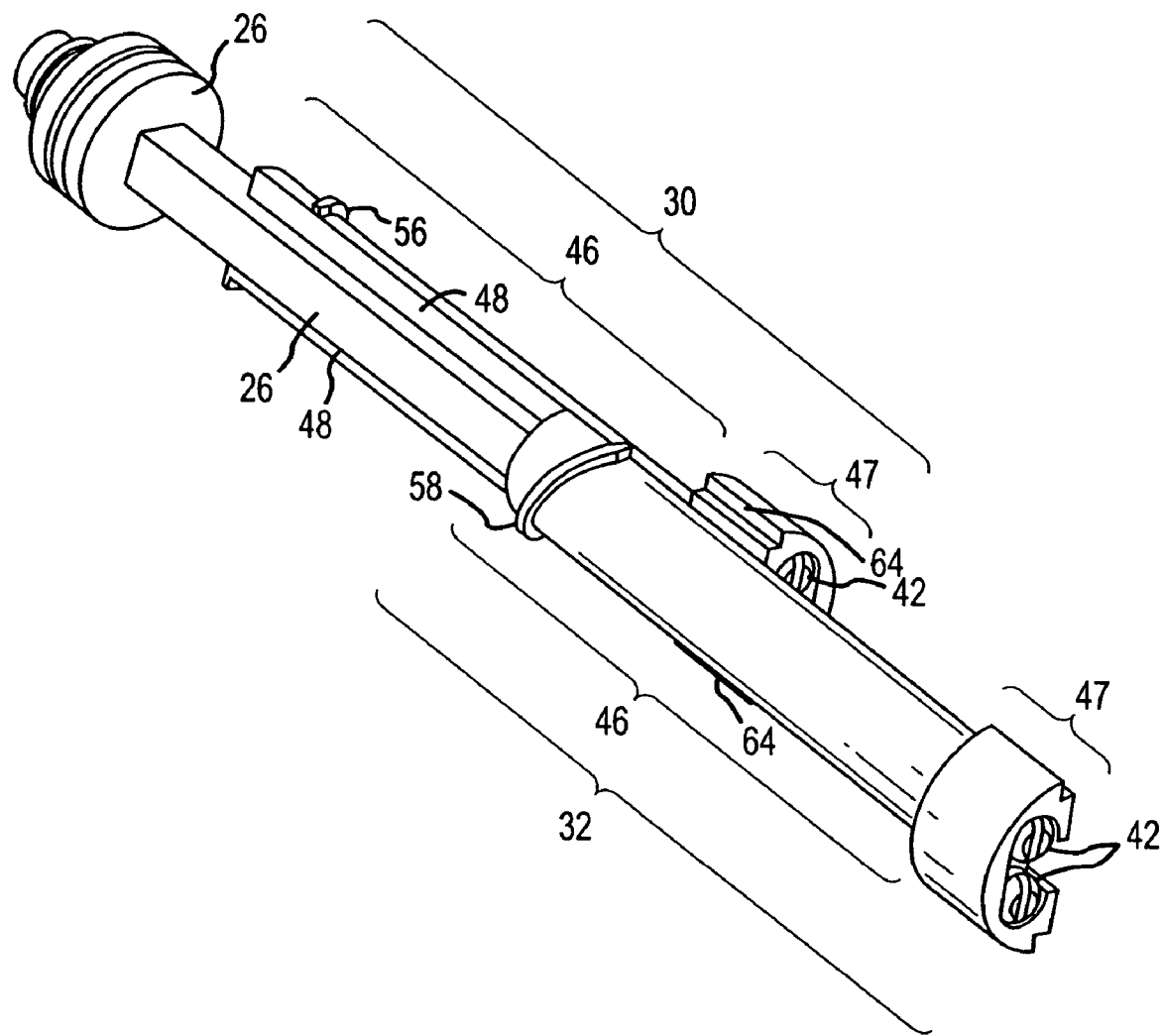
FIG. 13 is a left side isometric view of the slides displaced about the wire guide.

As indicated in FIG. 10, a right slide 30 and a left slide 32 are longitudinally displaceable within the handle 2 and about the proximal end of the wire guide 26. As shown in FIGS. 12 and 13, which are, respectively, a right side isometric view of the slides 30, 32 displaced about the wire guide 26 and a left side isometric view of the slides 30, 32 displaced about the wire guide 26, each slide 30, 32 has a planar slide face 48 that abuts and slideably displaces against the slide face 48 of the opposed slide 30, 32. Also, each slide 30, 32 has a channel 40 that combines with the channel 40 of the opposed slide 30, 32 to form a passage 40 through which the proximal end of the wire guide 26 passes as the slides 30, 32 displace about the wire guide 26. As shown in FIG. 10, the passage 40 formed by the channels 40 also provides a pathway along which the deflection wires 38a, 38b (represented by dashed lines in FIG. 10) travel from a proximal portion of the slides 30, 32, through the wire guide 26, and onward to the extreme distal end 14 of the catheter body 4.

As indicated in FIGS. 12 and 13, each slide 30, 32 has a half-cylinder distal portion 46 and a shorter and wider half-cylinder proximal portion 47. The right slide 30 has a right-handed thread 56 on its distal portion 46. Similarly, the left slide 32 has a left-handed thread 58 on its distal portion 46. Thus, as can be understood from FIG. 10, when the knob 10 is rotated in a clockwise direction relative to the handle grip 12, the right handed threads 62 within the knob 10 engage the right handed threads 56 of the right slide 30, and the left handed threads 64 within the knob 10 engage the left handed threads 58 of the left slide 32. As a result, the right slide 30 is distally displaced within the handle 2 and the left slide 32 is proximally displaced within the handle 2. Accordingly, the deflection wire 38a attached to the right slide 30 is pushed (i.e., subjected to a compressive force) and the deflection wire 38b attached to the left slide 32 is pulled (i.e., subjected to a tension force). Conversely, if the knob is rotated counterclockwise, the opposite displacement of the slides 30, 32 and deflection wires 38a, 38b will occur.

As indicated in FIG. 10, each deflection wire 38a, 38b is attached to the proximal portion 47 of its respective slide 30, 32 via retention screws 42. The retention screws, which are more clearly illustrated in FIGS. 12 and 13, are threadably mounted in the proximal portions 47.

As shown in FIGS. 12 and 13, each half-cylindrical proximal portion 47 of a slide 30, 32 has an upper and lower planar notch 64 adjacent their respective planar slide faces 47. The function of these notches 64 may be understood by referring to FIGS. 14 and 15.

Figure 14:
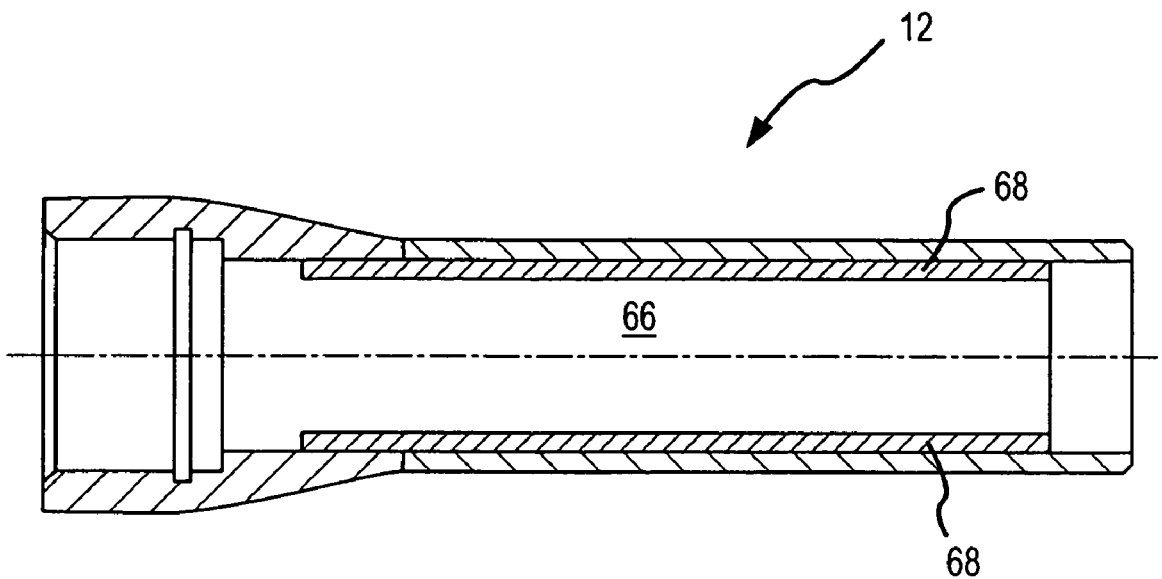
FIG. 14 is a longitudinal sectional elevation of the handle grip taken along section line CC in FIG. 7.
Figure 15:
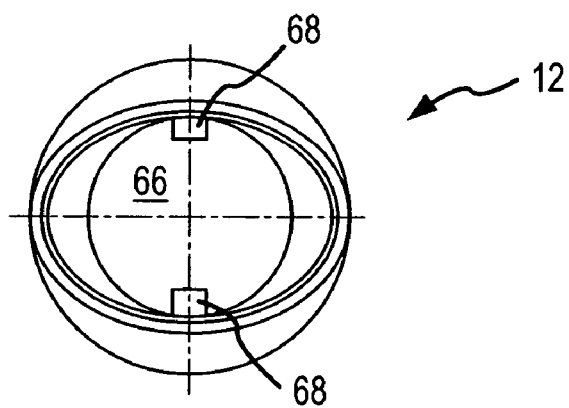
FIG. 15 is a latitudinal sectional elevation of the handle grip taken along section line DD in FIG. 8.

FIG. 14 is a longitudinal section elevation of the handle grip 12 taken along section line CC in FIG. 7. FIG. 15 is a latitudinal section elevation of the handle grip 12 taken along section line DD in FIG. 8. As shown in FIGS. 14 and 15, the handle grip 12 is one integral piece having an interior cylindrical void 66 in which the proximal portions 47 of the slides 30, 32 may displace as indicated in FIG. 10.

As shown in FIGS. 14 and 15, upper and lower ribs 68 extend from the walls that form the interior cylindrical void 66. The ribs 68 run longitudinally along a substantial portion of the cylindrical void's length. As can be understood from FIGS. 12-15, the upper planar notches 64 on the proximal portions 47 of the slides 30, 32 interface with, and displace along, the upper rib 68 as the slides 30, 32 displace within the cylindrical void 66. Similarly, the lower planar notches 64 on the proximal portions 47 of the slides 30, 32 interface with, and displace along, the lower rib 68 as the slides 30, 32 displace within the cylindrical void 66. Thus, the ribs 68 act as thrust surfaces for the slides 30, 32.

Figure 16:
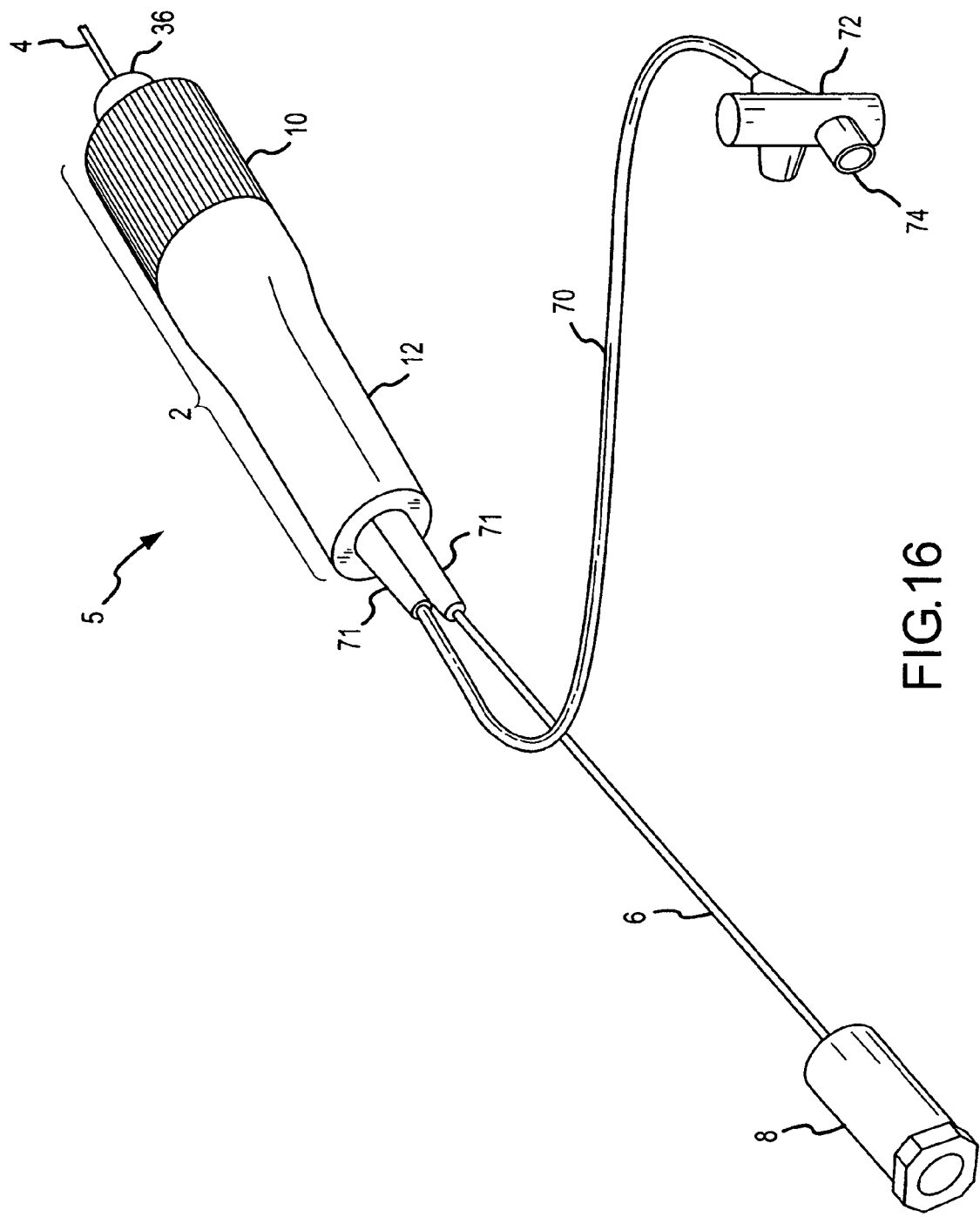
FIG. 16 is an isometric view of the distal end of a control handle for a catheter wherein the handle has a through lumen.

For a detailed discussion of another embodiment of the handle 2 depicted in FIGS. 7-15, reference is now made to FIG. 16. FIG. 16 is an isometric view of the distal end of a control handle 2 for a catheter 5 wherein the handle 2 and catheter body 4 have a through lumen 70. As shown in FIG. 16, in one embodiment, the lumen 70 and the electrical wire tube 6, which extends to the electrical connector 8, pass through strain reliefs 71 and into the proximal end of the handle grip 12. In one embodiment, the lumen 70 terminates at its proximal end with a stopcock 72. In one embodiment, the stopcock 72 has a hemostasis seal 74 that can be utilized for guide wire insertion. While a long flexible length of lumen 70, as depicted in FIG. 16, provides motion isolation while inserting contrast from a syringe, in one embodiment, the lumen 70 does not extend from the handle grip 12. Instead, the stopcock 72 or luer fitting is simply attached to the lumen 70 where it exits the proximal end of the handle grip 12.

Figure 17:
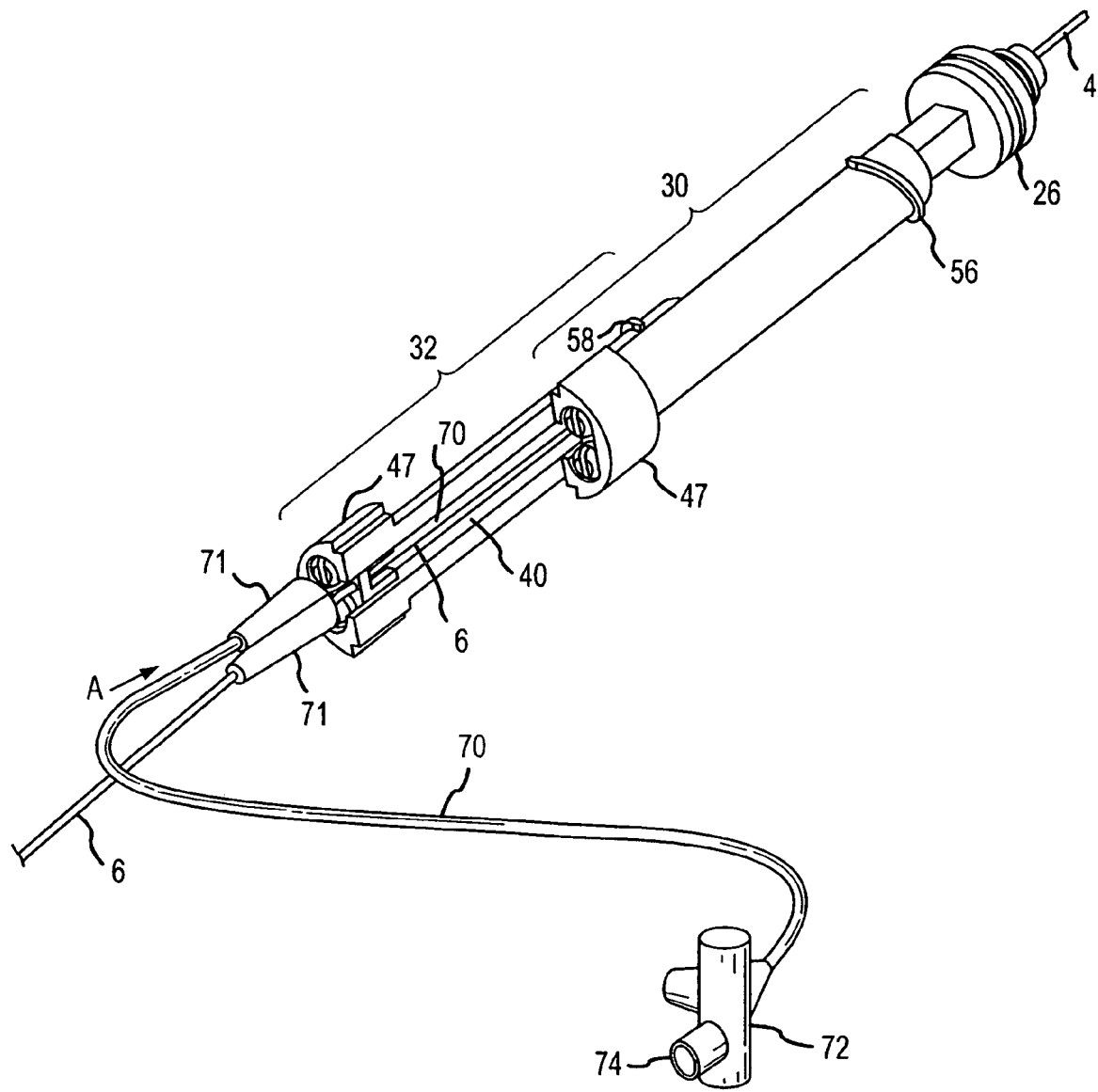
FIG. 17 is an isometric view of the slides, the wire guide, the wire tubing, and the lumen illustrating the path the lumen takes through the handle.
Figure 18:
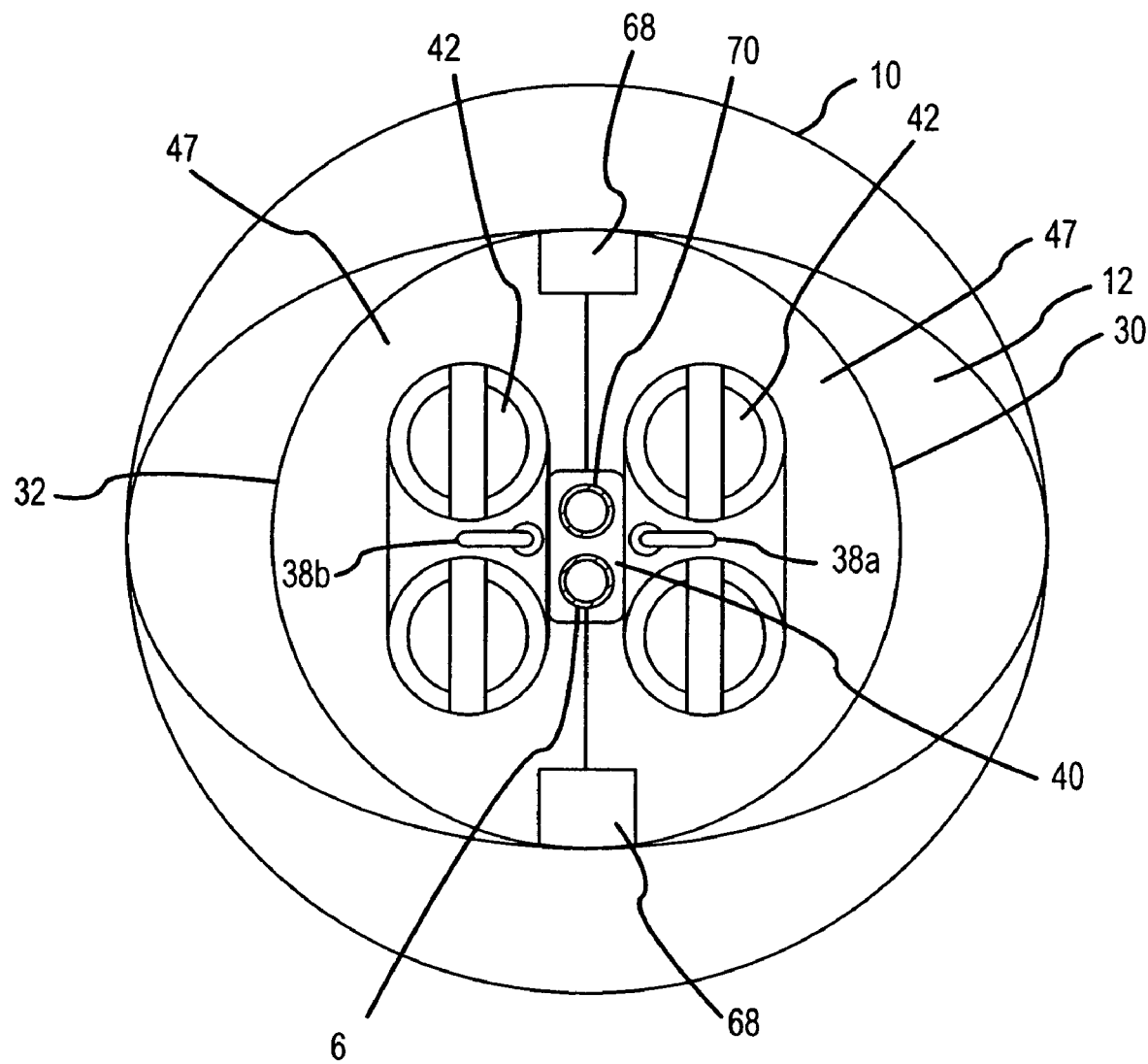
FIG. 18 is an elevation view of the extreme proximal end surfaces of the slides as viewed from arrow A in FIG. 17 and illustrating the path the lumen and wire tubing take into the passage formed by the channels of the slides.
Figure 19:
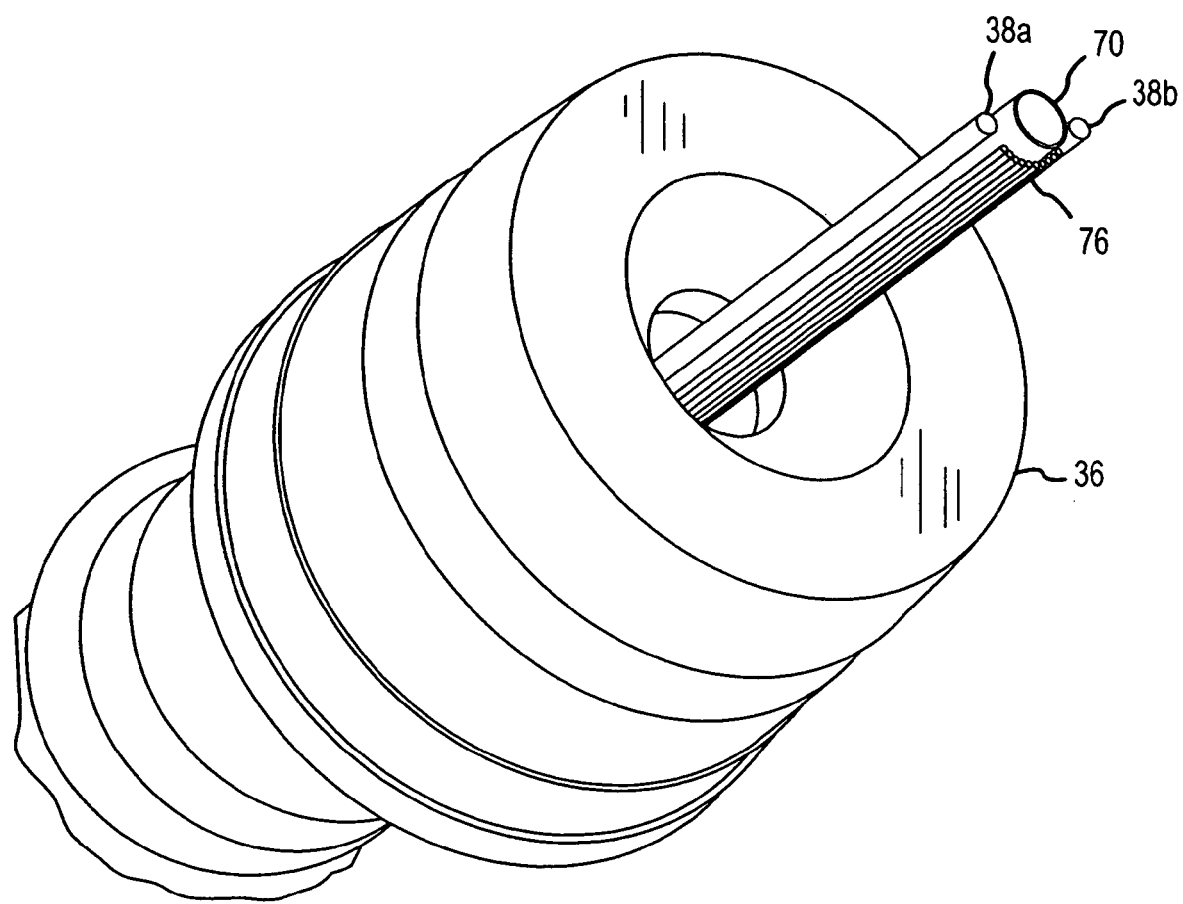
FIG. 19 is an isometric view of the lumen, deflection wires, and electrical wires of the tube exiting the catheter body-retaining nut on the distal end of the handle.

For a better understanding of the path of the lumen 70, reference is now made to FIGS. 17, 18 and 19. FIG. 17 is an isometric view of the slides 30, 32, the wire guide 26, the wire tubing 6, and the lumen 70 illustrating the path the lumen 70 takes through the handle 2. FIG. 18 is an elevation view of the extreme proximal end surfaces of the slides 30, 32 as viewed from arrow A in FIG. 17 and illustrating the path the lumen 70 and wire tubing 6 take into the passage 40 formed by the channels 40 of the slides 30, 32. FIG. 19 is an isometric view of the lumen 70, deflection wires 38a, 38b, and electrical wires 76 of the wire tube 6 exiting the catheter body-retaining nut 36 on the distal end of the handle 2.

As shown in FIGS. 17 and 18, the lumen 70 and the wire tubing 6 pass through their respective reliefs 71 and into the passage 40 formed by the channels 40 in each slide 30, 32. In one embodiment, soon after the wire tubing 6 and the lumen 70 enter the passage 40, the wires 76 of the wire tubing 6 exit the wire tubing 6 and are dispersed about the outer circumference of the lumen 70 as depicted in FIG. 19.

As illustrated in FIG. 17, in another embodiment, after the wire tube 6 and lumen 70 enter the passage 40, the wire tube 6 and the lumen 70 continue on their pathway to the distal end 14 of the catheter body 4 by passing, in a side-by-side arrangement, through the remainder of the passage 40 formed into the slides 30, 32 and into an internal passage that extends along the longitudinal axis of the wire guide 26. Near the end of the wire guide 26, the wire 76 exists the wire tube 6. The wire 76, lumen 70 and deflection wires 38a, 38b then pass into the catheter by exiting the catheter body-retaining nut 36 of the handle as indicated in FIG. 19.

Figure 20:
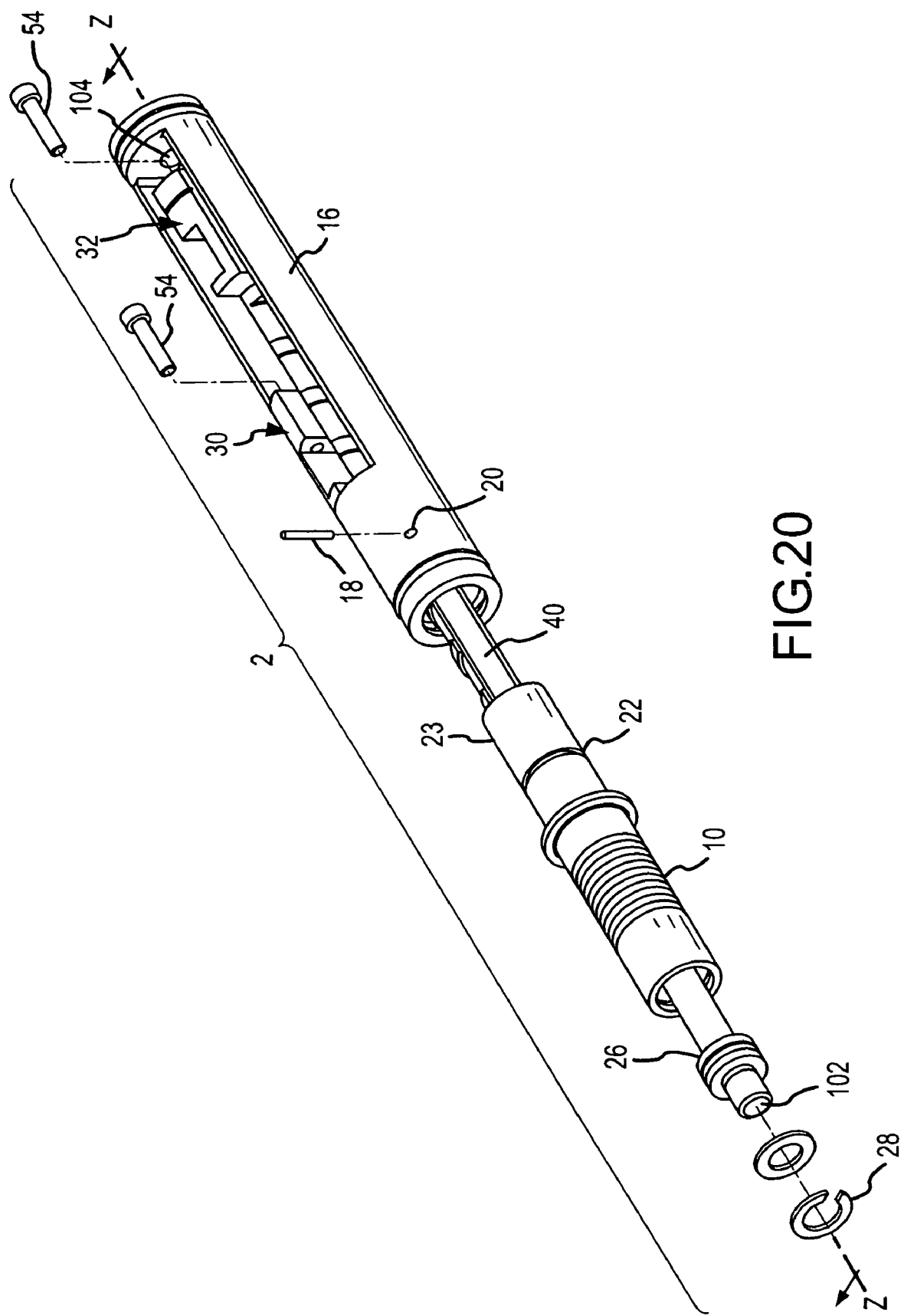
FIG. 20 is an isometric view of another embodiment of the handle exploded to show its various components.

For a detailed discussion of another embodiment of the handle 2, reference is now made to FIG. 20, which is an isometric view of the handle 2 exploded to show its various components. As can be understood from FIG. 20, the features of the handle 2 depicted in FIG. 20 are similar to the features of the handle depicted in FIG. 2, except the handle 2 depicted in FIG. 20 is configured to have a relatively large, generally uniform in diameter, pathway extend the full length of the handle 2 (i.e., from the distal opening 102 in the wire guide 26, through the passage 40 defined in the slides 30, 32 and through an exit hole 104 in the proximal end of the shaft 16).

Figure 21:
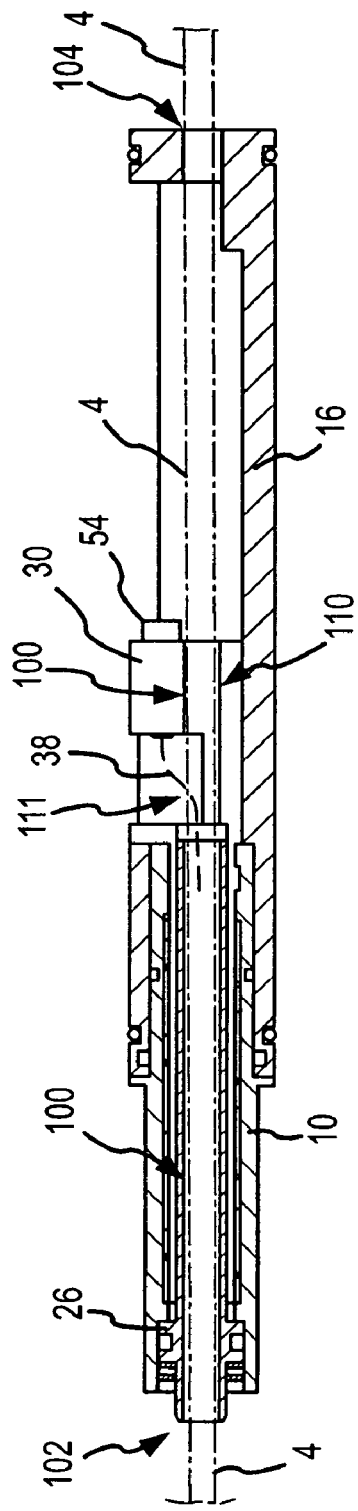
FIG. 21 is a longitudinal sectional elevation taken along section line ZZ in FIG. 20.

The configuration of the handle 2 that allows a relatively large generally uniform in diameter pathway to pass through the length of the handle 2, as depicted in FIG. 20, is more clearly shown in FIG. 21, which is a longitudinal sectional elevation taken along section line ZZ in FIG. 20. As illustrated in FIG. 21, in one embodiment, the pathway 100, which includes the passage through the wire guide 26 and the passage 40 through the slides 30, 32, is large enough that the catheter body 4 itself may pass through the pathway 100 and be connected to the proximal end of the shaft 16 at the exit hole 104. Thus, in one embodiment, to prevent the catheter body 4 from rotating with the adjusting knob 10, the catheter body 4 is affixed to the shaft 16 at the exit hole 104. In one embodiment, the catheter body 4 runs the full length of the handle 4 as depicted in FIG. 21, except the body 4 is affixed to the wire guide 26 at or near the distal opening 102. In other embodiments, the catheter body 4 is affixed to both the wire guide 26 at or near the distal opening 102 and the shaft 16 at the exit hole 104.

Figure 22:
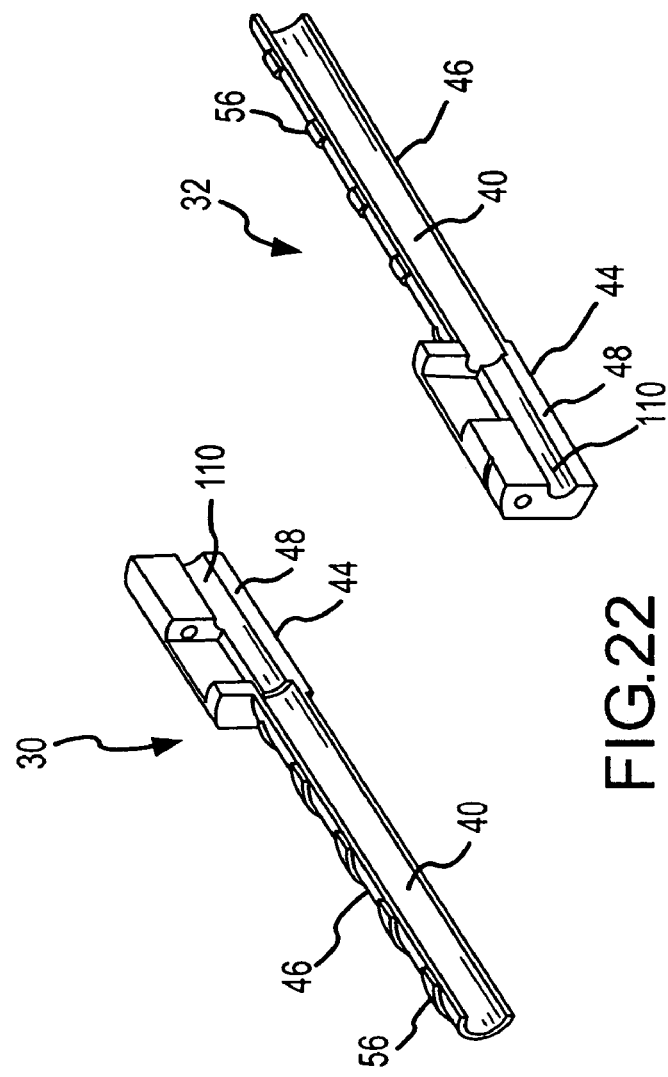
FIG. 22 is isometric views of the slides oriented to show their respective portions of the passage and their planar slide faces.

As can be understood from FIG. 21 and as more clearly depicted in FIG. 22, which is isometric views of the slides 30, 32 oriented to show their portions of the passage 40 and their planar slide faces 48, the passage 40 is large enough in diameter to displace over the outer diameter of the wire guide 26. As shown in FIGS. 21 and 22, a catheter body passage 110 passes through the proximal portion 44 of each slide 30, 32, thereby allowing the slides 30, 32 to displace back and forth over the outer surface of the catheter body 4.

As indicated in FIG. 21, in one embodiment, the catheter body 4 has an opening 111 in its wall that allows the wires 38 to exit the body 4 and connect to the slides 30, 32. In one embodiment, the wires 38 connect to the slides 30, 32 via tension adjustment screws 54 as previously discussed.

Due to the configuration of the slides 30, 32, the wire guide 26 and the shaft 16, the catheter body 4 may run uninterrupted the full length of the handle 2. As a result, electrical wiring 76 (see FIG. 19) and a lumen 70 may be routed the full length of the handle 2 by way of the body 4.

Figure 23:
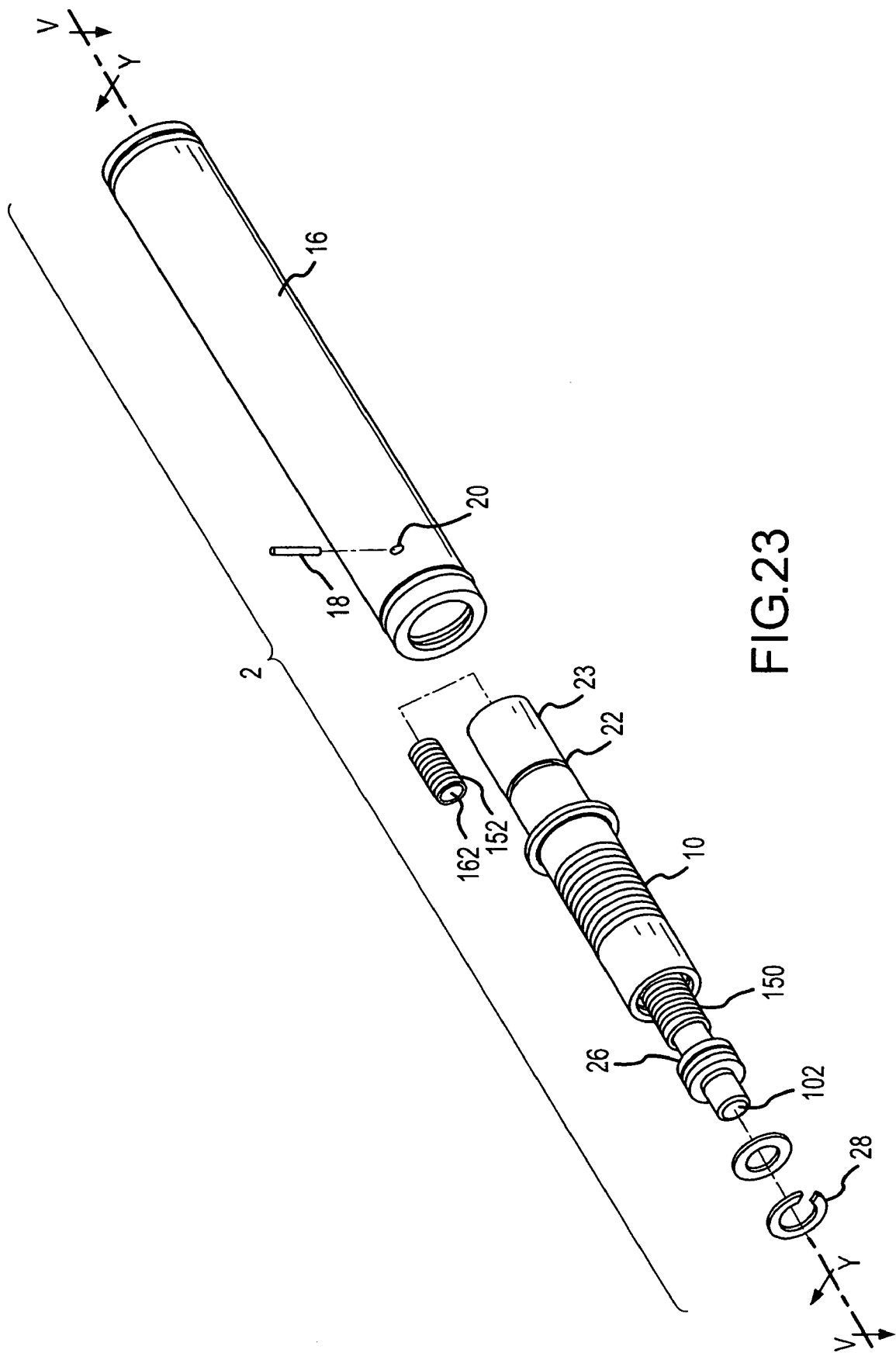
FIG. 23 is an isometric view of another embodiment of the handle exploded to show its various components.
Figure 24:
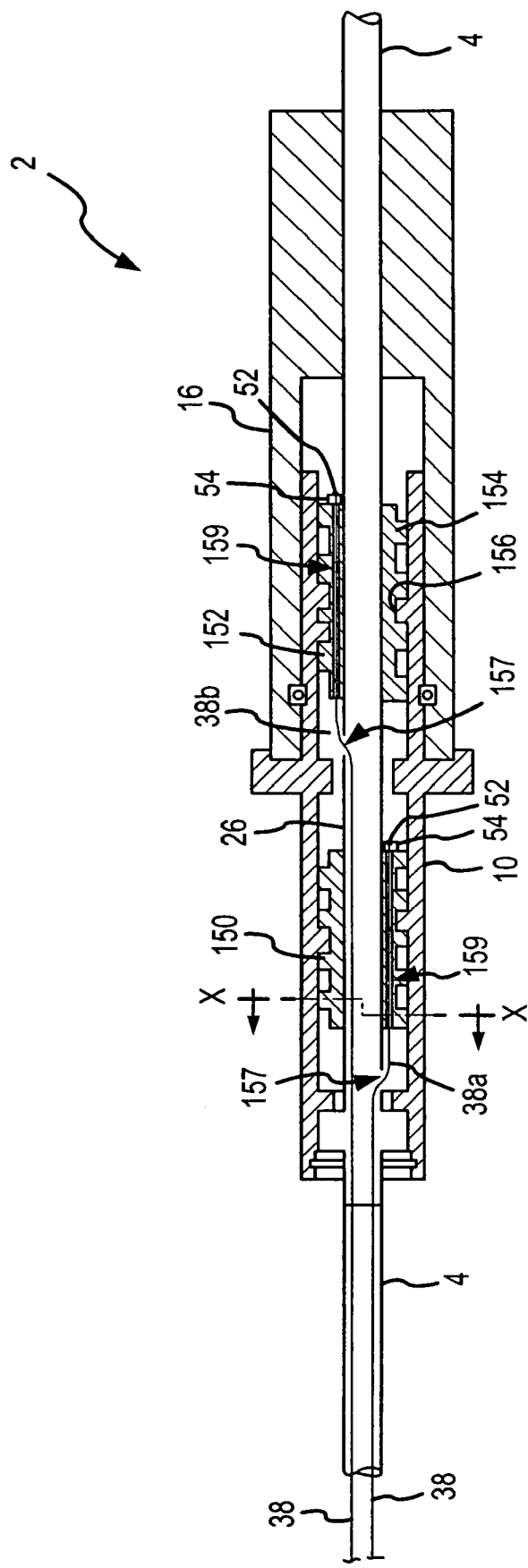
FIG. 24 is a longitudinal sectional elevation of the handle taken along section line YY of FIG. 23.

For a detailed discussion of another embodiment of the handle 2 of the present invention, reference is now made to FIGS. 23 and 24. FIG. 23 is an isometric view of the handle 2 exploded to show its various components. FIG. 24 is a longitudinal sectional elevation of the handle 2 taken along section line YY of FIG. 23. Generally speaking, the features of the handle 2 depicted in FIGS. 23 and 24 are similar to the features of the handle depicted in FIG. 20, except the two embodiments employ different slider arrangements. For example, the embodiments depicted in FIGS. 1-22 employ parallel slides or members 30, 32 (i.e., the slides 30, 32 exist within the handle 2 in a parallel or side-by-side arrangement). As will be understood from FIGS. 23 and 24 and the following figures, in the embodiment of the handle 2 depicted in FIGS. 23 and 24, the slides or members 150, 152 exist within the adjustment knob 10 in a series arrangement (i.e., the slides 150, 152 are not parallel or side-by-side to each other, but are oriented end-to-end along a longitudinal axis of the handle 2).

As shown in FIGS. 23 and 24, the adjusting knob 10 is pivotally coupled to the distal end of the mounting shaft (i.e., base portion) 16. The wire guide 26 extends through the center of the adjusting knob 10 and the mounting shaft 16. The catheter body 4 is coupled to the distal end of the wire guide 26 and, in one embodiment, extends through the wire guide 26 and out of the proximal end of the mounting shaft 16.

As shown in FIGS. 23 and 24, a distal slide 150 is located in a distal portion of the adjusting knob 10, and a proximal slide 152 is located in a proximal portion (i.e., hub portion 23) of the adjusting knob 10. As illustrated in FIG. 24, the outer surface of each slide 150, 152 has threads 154 that mate with threads 156 on an interior surface of the adjusting knob 10.

As illustrated in FIG. 24, each deflection wire 38*a*, 38*b* travels along the interior of the wire guide 26 until it exits the wire guide 26 at a hole 157 in the sidewall of the wire guide 26. Each deflection wire 38*a*, 38*b* then extends to the slide 150, 152 to which the deflection wire 38*a*, 38*b* is attached. In one embodiment, in order to attach to a slide 150, 152, a deflection wire 38*a*, 38*b* passes through a passage 159 in the slide 150, 152 and attaches to a hollow tension adjustment screw 54 via a knot 52 as previously described in this Detailed Description.

Figure 25:
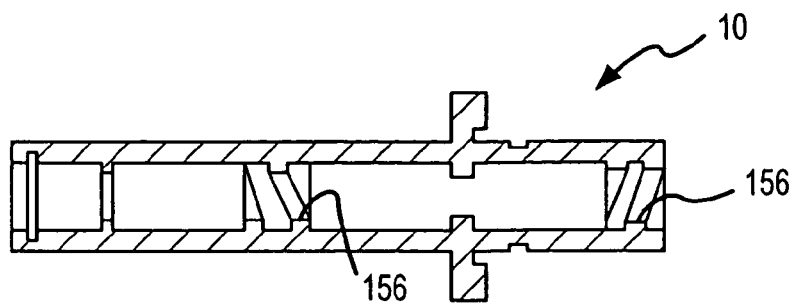
FIG. 25 is the same longitudinal sectional elevation of the adjusting knob as depicted in FIG. 24, except the adjusting knob is shown by itself.
Figure 26:
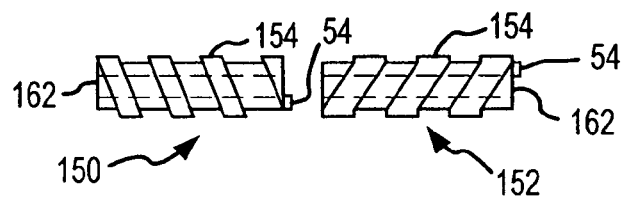
FIG. 26 is a side elevation of the slides.

For a better understanding of the orientation of the threads 154, 156, reference is now made to FIGS. 25 and 26. FIG. 25 is the same longitudinal sectional elevation of the adjusting knob 10 as it is depicted in FIG. 24, except the adjusting knob 10 is shown by itself. FIG. 26 is a side elevation of the slides 150, 152.

As shown in FIGS. 25 and 26, in one embodiment, the distal slide 150 has right hand threads 154 that engage right hand threads 156 in the distal portion of the adjusting knob 10, and the proximal slide 152 has left hand threads 154 that engage left hand threads 156 in the proximal portion of the adjusting knob 10. Thus, as can be understood from FIGS. 23-26, when the adjusting knob 10 is rotated relative to the mounting shaft 16 in a first direction about the longitudinal axis of the handle 2, the slides 150, 152 will converge along the wire guide 26, thereby causing the first wire 38 to be placed into tension and the second wire 38 to be compressed. As a result, the distal end 14 of the catheter body 4 will deflect in a first direction. Similarly, when the adjusting knob 10 is rotated in a second direction that is opposite from the first direction, the slides 150, 152 will diverge along the wire guide 26, thereby causing the first wire 38 to be compressed and the second wire 38 to be placed into tension. As a result, the distal end 14 of the catheter body 4 will deflect in a second direction generally opposite from the first direction.

Figures 27A, 27B:
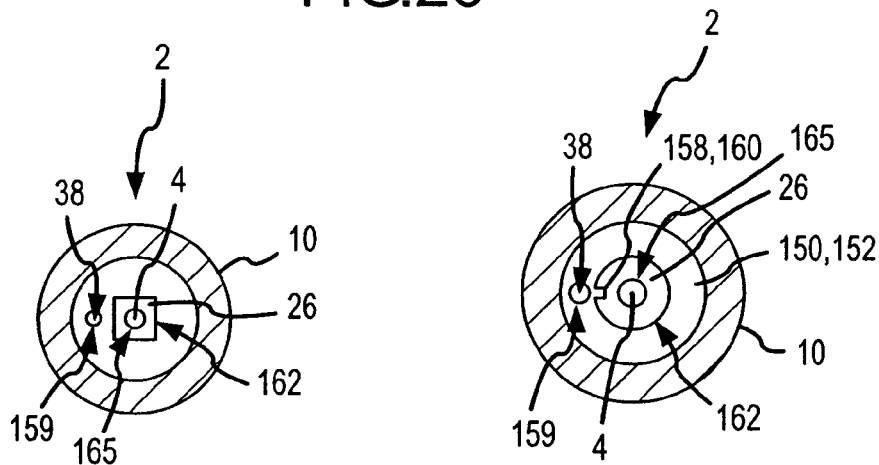
FIG. 27A is a latitudinal sectional elevation of the handle, as taken along section line XX in FIG. 24, wherein the wire guide has a square cross section.
FIG. 27B is the same latitudinal sectional elevation depicted in FIG. 27A, except the wire guide has a circular cross section and a key/groove arrangement.

In one embodiment, to prevent the slides 150, 152 from simply rotating around the wire guide 26 when the adjusting knob 10 is rotated, the slides 150, 152 and wire guide 26 are configured such that the slides 150, 152 will displace along the wire guide 26, but not rotationally around it. For example, as indicated in FIG. 27A, which is a latitudinal sectional elevation of the handle 2 as taken along section line XX in FIG. 24, the wire guide 26 has a square cross section that mates with a square hole 162 running the length of the slide 150, 152. The interaction between the square hole 162 and the square cross section of the wire guide 26 prevents a slide 150, 152 from rotating about the wire guide 26, but still allows the slide 150, 152 to displace along the length of the wire guide 26.

Figure 28:
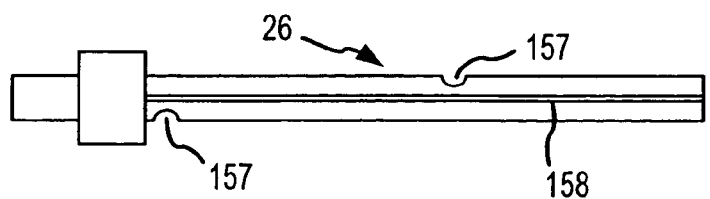
FIG. 28 is a side elevation of one embodiment of the wire guide equipped with a groove.

In another embodiment, as shown in FIG. 27B, which is the same latitudinal sectional elevation depicted in FIG. 27A, each slide 150, 152 has a hole 162 with a circular cross section. Each hole 162 runs the length of its respective slide 150, 152 and includes a key 160 that extends into the hole 162 from the interior circumferential surface of the hole 160. The key 160 engages a groove or slot 158 that runs along the length of the wire guide 26 as depicted in FIG. 28, which is a side elevation of one embodiment of the wire guide 26. The interaction between the key 160 and the slot 158 prevents a slide 150, 152 from rotating about the wire guide 26, but still allows the slide 150, 152 to displace along the length of the wire guide 26.

As shown in FIGS. 27A and 27B, a hollow shaft 165 extends through the wire guide 26. This allows a catheter body 4 with a lumen to extend completely through the handle 2 as shown in FIG. 24.

For a detailed discussion of another embodiment of the handle 2 that is similar to the embodiment depicted in FIG. 23, reference is now made to FIGS. 29 and 30. FIG. 29 is a longitudinal sectional elevation of the handle 2 as if taken through section line YY of FIG. 23. FIG. 30 is a longitudinal sectional plan view of the handle 2 as if taken through section line VV in FIG. 23 and wherein section line VV forms a plane that is perpendicular to the plane formed by section line YY in FIG. 23.

As illustrated in FIGS. 29 and 30, the handle 2 includes an adjusting knob 10 pivotally coupled to the distal end of the mounting shaft (i.e., base portion) 16. In one embodiment, the adjusting knob 10 includes a proximal end 170, a distal end 172 and a threaded shaft 173, which is connected to the proximal end 170 and extends distally along the longitudinal axis of the adjusting knob 10. The threaded shaft 173 includes a distal end 174, a proximal end 176, a series of right hand threads 178 along a distal portion of the shaft 173, and a series of left hand threads 180 along a proximal portion of the shaft 173.

As shown in FIGS. 29 and 30, a distal slide 150 is located in a distal portion of the adjusting knob 10, and a proximal slide 152 is located in a proximal portion (i.e., hub portion 23) of the adjusting knob 10. Each slide has a hole 155 through which the threaded shaft 173 passes. The inner circumferential surface of the hole 155 for the distal slide 150 has right hand threads that mate with the right hand threads 178 on the distal portion of the shaft 173. Similarly, the inner circumferential surface of the hole 155 for the proximal slide 152 has left hand threads that mate with the left hand threads 180 on the proximal portion of the shaft 173. In other embodiments, the locations for the left and right threads are reversed.

As can be understood from FIGS. 29, 30 and 31, which is an isometric view of one embodiment of the wire guide 26, a hollow center shaft 182 extends from the distal end of the wire guide 26, through the threaded shaft 173 of the adjustment knob 10, and to the proximal end of the base shaft 16. Thus, in one embodiment, a catheter body 4 may be routed through the lumen 165 of the wire guide's hollow center shaft 182 to exit the proximal end of the handle 2, as illustrated in FIGS. 29 and 30.

As illustrated in FIG. 29, each deflection wire 38a, 38b travels along the interior of the wire guide 26 until it exits the wire guide 26 at a hole 157 in the sidewall of the wire guide 26. Each deflection wire 38a, 38b then extends to the slide 150, 152 to which the deflection wire 38a, 38b is attached. In one embodiment, in order to attach to a slide 150, 152, a deflection wire 38a, 38b passes through a passage 159 in the slide 150, 152 and attaches to a hollow tension adjustment screw 54 via a knot 52 as previously described in this Detailed Description.

In one embodiment, as shown in FIG. 29, the deflection wire 38b leading to the proximal slide 152 passes through a second passage 161 in the distal slide 150. The second passage 161 has sufficient clearance that the passage 161 may easily displace along the wire 38b when the distal slide 150 displaces distally and proximally. The second passage 161 serves as a guide that stiffens the wire 38b and helps to reduce the likelihood that the wire 38b will bend when compressed.

As can be understood from FIGS. 29 and 30, when the adjusting knob 10 is rotated relative to the mounting shaft 16 in a first direction about the longitudinal axis of the handle 2, the slides 150, 152 will converge along the threaded shaft 173, thereby causing the first wire 38a to be placed into tension and the second wire 38b to be compressed. As a result, the distal end 14 of the catheter body 4 will deflect in a first direction. Similarly, when the adjusting knob 10 is rotated in a second direction that is opposite from the first direction, the slides 150, 152 will diverge along the threaded shaft 173, thereby causing the first wire 38a to be compressed and the second wire 38b to be placed into tension. As a result, the distal end 14 of the catheter body 4 will deflect in a second direction generally opposite from the first direction.

In one embodiment, to prevent the slides 150, 152 from simply rotating with the threaded shaft 173 within the adjusting knob 10 when the adjusting knob 10 is rotated, the slides 150, 152 and wire guide 26 are configured such that the slides 150, 152 will displace along the threaded shaft 173, but not rotationally within the adjusting knob 10. For example, as indicated in FIGS. 31 and 32, which is a latitudinal sectional elevation of the handle 2 as taken along section line WW in FIG. 29, the wire guide 26 has right and left semicircular portions 190 that oppose each other and extend along the length of the hollow center shaft 182 of the wire guide 26. As shown in FIG. 32, the generally planar opposed faces 192 of the semicircular portions 190 abut against the generally planar side faces 194 of the slides 150, 152. This interaction prevents a slide 150, 152 from rotating within the adjustment knob 10 when the knob 10 is rotated, but still allows the slide 150, 152 to displace along the length of the threaded shaft 173.

Figure 36:
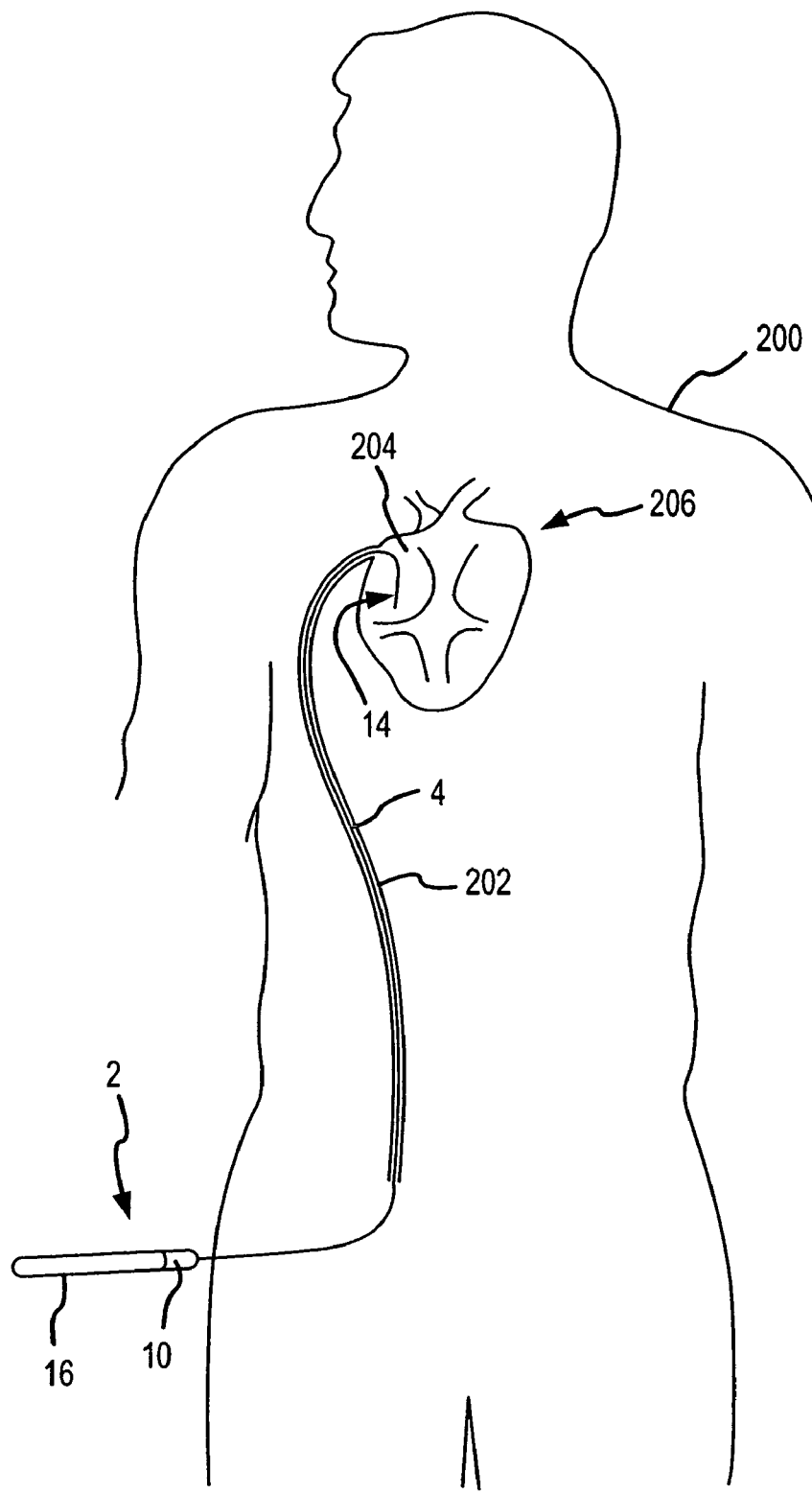
FIG. 36 is a diagrammatic illustration of the control handle of the subject invention being employed in a surgical procedure on a patient.

As can be understood from FIG. 36, which is a diagrammatic illustration of the control handle 2 of the subject invention being employed in a surgical procedure on a patient 200, the distal end 14 of the catheter body 4 is inserted into the patient 200 (e.g., intravenously via a body lumen 202 of the patient 200, percutaneously, or via other avenues for entering the patient's body). The distal end 14 of the catheter body 4 is advanced until positioned in a selected location within the patient 200 (e.g., within a chamber 204 of the patient's heart 206 or other organ, with a body cavity of the patient, etc.). The distal end of the catheter body 4 is then deflected by rotating the adjustment knob 10 about a longitudinal axis of a base portion 16. As can be understood from FIGS. 1-35, this causes the slides 30, 32 within the handle 2 to displace along the longitudinal axis in opposite directions. Since each slide 30, 32 is coupled to its respective deflection wire 38 and each deflection wire 38 runs through the catheter body 4 and is coupled to the distal end 14, the distal end 14 of the catheter body 4 is deflected.

Although the present invention has been described with reference to preferred embodiments, persons skilled in the art will recognize that changes may be made in form and detail without departing from the spirit and scope of the invention.

We claim:

1. A handle for controlling distal end deflection of a catheter body, wherein the catheter body includes first and second deflection wires, the handle comprising: a slide base including a first end, a second end, and a slide compartment longitudinally extending through at least a portion of the slide base; an adjustment knob rotateably connected to the first end of the slide base and including a hole extending through the knob, wherein at least a portion of an inner diameter of the hole includes an internal right thread and an internal left thread; a first slide located in the slide compartment, adapted to be coupled to the first deflection wire and including an external right thread; and a second slide located in the slide compartment, adapted to be coupled to the second deflection wire and including an external left thread, wherein the internal threads of the knob engage the threads of the slides and rotation of the adjustment knob causes the slides to displace in opposite directions within the slide compartment.

2. The handle of claim 1, further comprising a handle cover, wherein the slide base is received within the handle and the slide compartment is enclosed via the cover.

3. The handle of claim 1, further comprising a wire guide, wherein at least a portion of the guide resides within the hole of the knob and wherein the first and second deflection wires pass through the wire guide.

4. The handle of claim 3, wherein portions of the first and second slides displace along an outer surface of the wire guide.

5. The handle of claim 4, wherein an end of the wire guide is coupled to the catheter body.

6. The handle of claim 4, wherein the first end of the slide base is a distal end and the second end of the slide base is a proximal end.

7. The handle of claim 6, wherein a proximal end of the catheter body is coupled to a distal end of the wire guide.

8. The handle of claim 1, wherein portions of the first and second slides displace along an outer surface of the catheter body.

9. The handle of claim 8, wherein a proximal end of the catheter body is coupled to a proximal end of the handle.

10. The handle of claim 8, further comprising a wire guide positioned between inner surfaces of the slides and an outer surface of the catheter body.

11. The handle of claim 1, wherein the first slide forms a first point of contact with a slide frame and the second slide forms a second point of contact with the slide frame, wherein the points of contact act to prevent the slides from rotationally displacing within the slide compartment when the adjustment knob is rotated.

12. The handle of claim 11, wherein the first point of contact exists between a first side of a slide frame rail and a first half of a groove formed between the first and second slides, wherein the second point of contact exits between a second side of the rail and a second half of the groove.

13. The handle of claim 11, wherein the first point of contact exists between a first planar surface of the compartment and a planar surface of the first slide, wherein the second point of contact exists between a second planar surface of the compartment and a planar surface of the second slide.

14. The handle of claim 1, wherein each slide includes, and threadably receives, a bolt having a longitudinal axis, wherein each slide's respective deflection wire passes through the longitudinal axis of the respective bolt.

15. A handle for controlling distal end deflection of a catheter body, wherein the catheter body includes a first deflection wire and a second deflection wire, the handle comprising:
a first handle portion rotateably coupled to a second handle portion; and
a first member and a second member longitudinally displaceable within the handle,
wherein the first member is adapted to couple to the first deflection wire, the second member is adapted to couple to the second deflection wire, rotation of the first handle portion relative to the second handle portion causes the members to displace in opposite directions, and rotational movement of the first handle portion is transmitted into linear movement of the members via a threaded arrangement.

16. The handle of claim 15, wherein the displacement of the members is along a longitudinal axis of the second handle portion.

17. The handle of claim 15, wherein the rotation of the first handle portion is about a longitudinal axis of the second handle portion.

18. The handle of claim 15, wherein the threaded arrangement includes a first right thread along an outer circumferential surface of the first member, a first left thread along an outer circumferential surface of the second member, and a second right thread and a second left thread along an inner circumferential surface of the first handle portion, wherein the left threads are in engagement with each other and the right threads are in engagement with each other.

19. The handle of claim 18, wherein the second right thread is located in a proximal portion of the first handle portion and the second left thread is located in a distal portion of the first handle portion.

20. The handle of claim 18, wherein the second right thread is located in a distal portion of the first handle portion and the second left thread is located in a proximal portion of the first handle portion.

21. The handle of claim 18, wherein the first and second members are positioned relative to each other within the first handle portion in a generally end-to-end arrangement.

22. The handle of claim 18, wherein the second right thread and the second left thread are located generally at the same location within the first handle portion such that the second left thread and the second right thread form a bi-directional threading configuration along the inner circumferential surface of the first handle portion.

23. The handle of claim 22, wherein the first and second members are positioned relative to each other within the first handle portion in a generally side-by-side arrangement.

24. The handle of claim 23, wherein the each member has a generally planar side face that slideably abuts against the generally planar side face of the other member as the members displace oppositely relative to each other.

25. The handle of claim 23, wherein each member has a distal portion that carries the member's respective thread and a proximal portion that has a generally planar face for slideably abutting against a generally planar portion of a slot in the second handle portion.

26. The handle of claim 23, wherein each member has a distal portion that carries the member's respective thread and a proximal portion that has a first feature for slideably abutting against a second feature in a cavity within the second handle portion, thereby preventing the member from rotationally displacing within the cavity when the first handle portion is rotated relative to the second handle portion.

27. The handle of claim 15, wherein the threaded arrangement includes a first right thread along an inner circumferential surface of the first member, a first left thread along an inner circumferential surface of the second member, and a second right thread and a second left thread along an outer circumferential surface of the first handle portion, wherein the left threads are in engagement with each other and the right threads are in engagement with each other.

28. The handle of claim 27, wherein the second right thread and the second left thread are located generally at the same location on the first handle portion such that the second left thread and the second right thread form a bi-directional threading configuration along the outer circumferential surface of the first handle portion.

29. The handle of claim 28, wherein the first and second members are positioned relative to each other within the first handle portion in a generally side-by-side arrangement.

30. The handle of claim 29, wherein the each member has a generally planar side face that slideably abuts against the generally planar side face of the other member as the members displace oppositely relative to each other.

31. The handle of claim 29, wherein each member has a distal portion that carries the member's respective thread and a proximal portion that has a generally planar face for slideably abutting against a generally planar portion of a slot in the second handle portion.

32. The handle of claim 29, wherein each member has a distal portion that carries the member's respective thread and a proximal portion that has a first feature for slideably abutting against a second feature in a cavity within the second handle portion, thereby preventing the member from rotationally displacing within the cavity when the first handle portion is rotated relative to the second handle portion.

33. The handle of claim 15, wherein the members displace along an outer surface of the catheter body.

34. The handle of claim 15, further comprising a wire guide extending through at least a portion of the first handle portion, wherein the members displace along an outer surface of the wire guide.

35. The handle of claim 34, wherein the wire guide has a non-circular latitudinal cross-section.

36. The handle of claim 35, wherein the cross-section is generally rectangular.

37. The handle of claim 34, wherein the wire guide has a first feature for engaging a second feature of the first member, thereby preventing the rotational displacement of the first member about the wire guide.

38. The handle of claim 37, wherein the first feature is a groove and the second feature is a key for being slideably received in the groove.

39. The handle of claim 15, wherein the first handle portion includes a cavity and a threaded shaft extending through the cavity and along a longitudinal axis of the first handle portion.

40. The handle of claim 39, wherein the threaded shaft includes a first outer circumferential portion with right hand threads and a second outer circumferential portion with left hand threads.

41. The handle of claim 40, wherein the first member and the second member each include a hole whereby the threaded shaft may pass through each member, wherein the hole of the first member includes a right hand thread on an inner circumferential surface of said hole for engaging the right hand threads of the threaded shaft, and the hole of the second member includes a left hand thread on an inner circumferential surface of said hole for engaging the left hand threads of the threaded shaft.

42. The handle of claim 41, further comprising a wire guide including a feature adapted to prevent the members from rotationally displacing about the threaded shaft when the first handle portion is rotated relative to the second handle portion.

43. The handle of claim 42, wherein the feature is a generally planar portion extending longitudinally along the cavity and against which a generally planar portion of each member may slideably displace.

44. The handle of claim 15, wherein each member includes a coupling arrangement between the member and its respective deflection wire that allows deflection wire tension to be adjusted prior to displacing the member.

45. The handle of claim 15, wherein a coupling arrangement between each member and its respective deflection wire allows a member to displace relative to its respective deflection wire when the member is displacing distally, but requires the wire to displace with the member when the member is displacing proximally.

* * * * *